(12) United States Patent
Johnston et al.

(10) Patent No.: US 6,682,516 B2
(45) Date of Patent: Jan. 27, 2004

(54) LEG GASKETING INDEX FOR ABSORBENT UNDERGARMENTS

(75) Inventors: Lee W. Johnston, Suwanee, GA (US); Kenneth John Molee, Suwanee, GA (US); Stacy Jean Driskell, Loganville, GA (US); John D. Litvay, Duluth, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 66 days.

(21) Appl. No.: 10/046,553

(22) Filed: Jan. 16, 2002

(65) Prior Publication Data

US 2003/0171731 A1 Sep. 11, 2003

(51) Int. Cl.[7] ................................................ A61F 13/20
(52) U.S. Cl. ............................ 604/385.28; 604/385.24; 604/385.01
(58) Field of Search ........................ 604/385.01, 385.24, 604/385.28, 385.27, 385.25, 385.26

(56) References Cited

U.S. PATENT DOCUMENTS

| | | |
|---|---|---|
| 3,860,003 A | 1/1975 | Buell |
| 4,081,301 A | 3/1978 | Buell |
| 4,515,595 A | 5/1985 | Kievit et al. |
| 4,610,678 A | 9/1986 | Weisman et al. |
| 4,695,278 A | 9/1987 | Lawson |
| 4,795,454 A | 1/1989 | Dragoo |
| 4,808,177 A | 2/1989 | DesMarais et al. |
| 4,816,025 A | 3/1989 | Foreman |
| 4,919,738 A | 4/1990 | Ball et al. |
| 4,938,755 A | 7/1990 | Foreman |
| 4,990,541 A | 2/1991 | Nielsen et al. |
| 5,137,537 A | 8/1992 | Herron et al. |
| 5,147,345 A | 9/1992 | Young et al. |
| 5,275,590 A | 1/1994 | Huffman et al. |
| 5,281,207 A | 1/1994 | Chmielewski et al. |
| H1565 H | 7/1996 | Brodof et al. |
| 6,068,620 A | 5/2000 | Chmielewski |
| 6,123,694 A | 9/2000 | Pieniak et al. |
| 6,176,952 B1 | 1/2001 | Maugans et al. |

*Primary Examiner*—Weilun Lo
*Assistant Examiner*—Michele Kidwell

(57) ABSTRACT

An absorbent garment having standing leg gathers with improved leak containment capabilities, a method of making the absorbent garment, and a method of determining the leak containment capability of a standing leg gather are disclosed herein. In a first aspect, a method of determining a Leg Gasketing Index is disclosed herein and includes elongating a section of a standing leg gather and measuring the resulting elastic contractile force. In a second aspect, the present invention relates to an absorbent garment including standing leg gathers having a mean Total Leg Gasketing Index over three elongation cycles of at least about 4.75 kg*mm.

71 Claims, 8 Drawing Sheets

SECTION 332-332

SECTION 334-334

LEG GASKETING INDEX FOR ABSORBENT UNDERGARMENTS

FIELD OF THE INVENTION

The present invention relates generally to preventing leakage in absorbent garments and more specifically to a standing leg gather having a high leak containment ability. The present invention also relates to an absorbent garment having high leak containment properties.

BACKGROUND OF THE INVENTION

Disposable absorbent garments, such as disposable diapers and training pants, are commonly used in the hygienic care of infants and incontinent adults. These garments typically include an absorbent core integrated between a liquid-impervious backsheet and a liquid-pervious topsheet. Disposable absorbent garments can also have other features incorporated into their design, such as fastening tabs, an elastic waist band, soft side seams, and the like.

Although the absorbent core typically is capable of absorbing and storing a relatively large quantity of body exudates, the rate at which body exudates are expelled, as well as the quantity of body exudates expelled, often can overwhelm the absorbent action of the absorbent core, resulting in unabsorbed body waste and fluids between the body of the wearer and the surface of the topsheet. Accordingly, many absorbent garments include standing leg gathers and other types of leg gathers to form leg-encircling barriers to the leakage of unabsorbed body exudates from the absorbent garment. The containment capabilities of these standing leg gathers typically are enhanced by including elastic elements along the length of the standing leg gather to provide a contractile force that further constricts the standing leg gather against the leg of the wearer, thereby reducing the ability of unabsorbed exudates to escape from between the leg of the wearer and the edge of the standing leg gather in contact with the leg of the wearer. In effect, the standing leg gather is intended to form a "gasket" between the body of the wearer and the absorbent garment, thereby inhibiting the leakage of body exudates.

SUMMARY OF THE INVENTION

While the use of standing leg gathers in absorbent garments for enhanced leak containment is known, it is desired to more particularly define the leak containment ability of standing leg gathers to determine those standing leg gathers that are better suited for use in containing body exudates in absorbent garments. The present invention seeks to determine the leak containment ability of standing leg gathers by providing an objective standing leg gather test method and to provide a standing leg gather having improved performance, as determined by the test method.

It would be desirable to provide standing leg gathers having superior leak containment properties. It also would be desirable to quantify the ability of a standing leg gather to seal against a leg of a wearer to prevent or minimize leakage of body fluids.

In accordance with at least one embodiment of the present invention, a disposable absorbent garment is provided. The absorbent garment comprises a back sheet, a top sheet, and an absorbent core disposed between the back sheet and the top sheet. The absorbent garment further comprises at least one longitudinally extending, elasticized standing leg gather disposed laterally from a longitudinal centerline of the garment, the at least one elasticized standing leg gather including at least one elastic element for distributing elastic contractile forces generated by the at least one elastic element along a substantial portion of a horizontal extent of each standing leg gather. In accordance with embodiments of the present invention, the at least one standing leg gather has a mean Total Leg Gasketing Index over three elongation cycles of at least about 4.75 kg*mm.

In accordance with other embodiments of the present invention, the standing leg gather has Summation Leg Gasketing Index over three cycles at 195% elongation of at least about 25 kg*mm. In accordance with another embodiment, the standing leg gather has a first cycle mean partial Leg Gasketing Index of at least about 23 kg*mm.

In accordance with yet another embodiment of the present invention, there is provided a method of determining the Leg Gasketing index of an elasticized standing leg gather disposed laterally from a longitudinal centerline of an absorbent garment, the standing leg gather including at least one elastic element for distributing elastic contractile forces generated by the at least one elastic element along a substantial portion of a horizontal extent of the standing leg gather. The method includes obtaining a section of the standing leg gather, the section having a height and an unloaded length, determining the height of the section of the standing leg gather, elongating the section of the standing leg gather from the unloaded length to a first elongation, determining a first elastic contractile force exhibited by the section of the standing leg gather at the first elongation, and calculating a first Leg Gasketing Index by multiplying the height of the section by the first elastic contractile force.

In accordance with another embodiment of the invention, there is provided a method of making an absorbent garment that includes providing a top sheet material, a back sheet material, and an absorbent core, and disposing the absorbent core between the top sheet material and the back sheet material. The method also includes providing at least one longitudinally extending, elasticized standing leg gather, and disposing the standing leg gather laterally from a longitudinal centerline of the garment, whereby the at least one standing leg gather includes at least one elastic element, and it has a mean Total Leg Gasketing Index over three elongation cycles of at least about 4.75 kg*mm.

BRIEF DESCRIPTION OF THE DRAWINGS

The present invention can be understood more completely by reading the following detailed description, in conjunction with the accompanying drawings, in which.

DETAILED DESCRIPTION OF THE PREFERRED EMBODIMENTS

Figure 1:
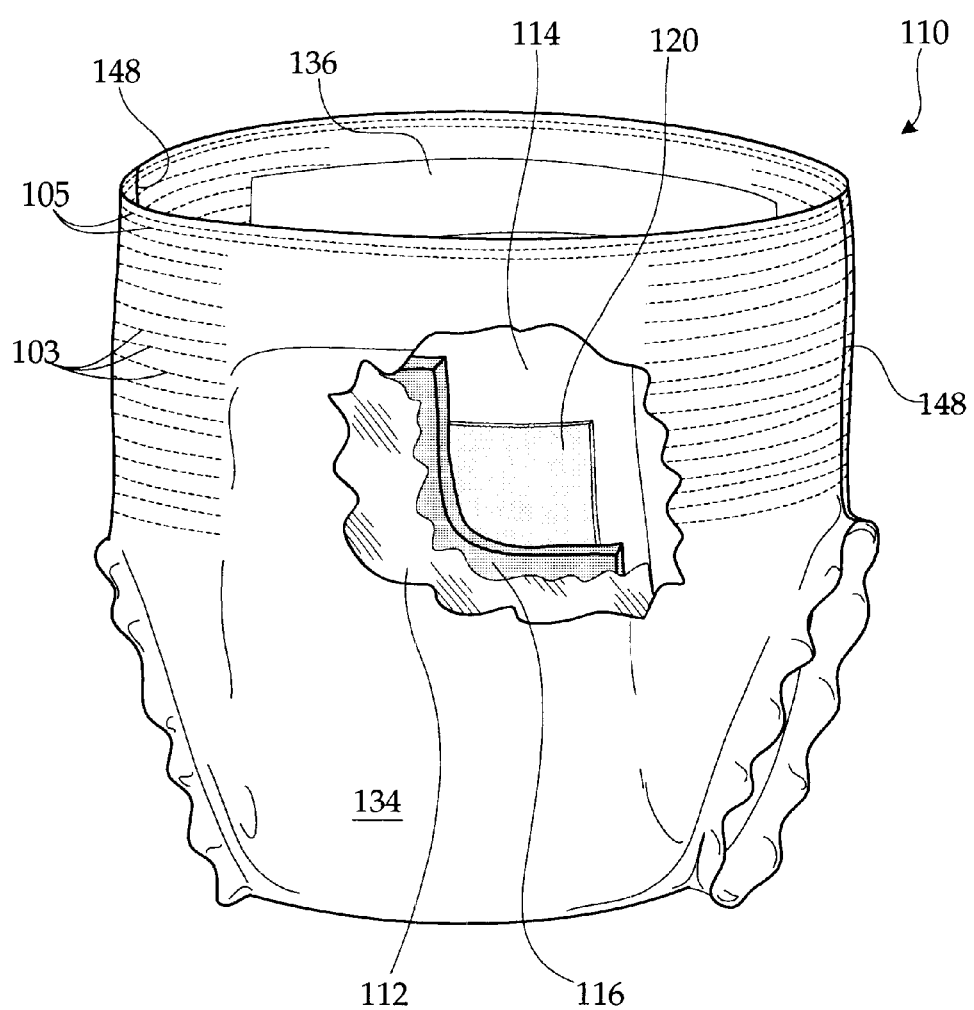
FIG. 1 is a perspective view of a disposable absorbent garment, configured as a training pant, in accordance with at least one embodiment of the present invention, where the disposable absorbent garment is depicted generally as it appears when being worn.

"Garment," as used herein, refers to articles and garments that absorb and contain body exudates, and more specifically refers to articles and garments that are placed against or in proximity to the body of the wearer to absorb and contain the various exudates discharged from the wearer's body. A non-exhaustive list of examples of "absorbent articles" and garments includes training pants, diapers, diaper covers, disposable diapers, feminine hygiene products, and adult incontinence products. The invention can be used with all of the foregoing classes of absorbent articles and garments, without limitation, whether disposable or otherwise. Furthermore, the invention will be understood to encompass, without limitation, all classes and types of absorbent articles and garments, including those described above.

Throughout this description, the expressions "upper layer," "lower layer," "above" and "below," "top" and "bottom," which refer to the various components included in the absorbent garments of the invention (including the layers surrounding the absorbent core units), as well as the depiction in the drawings of certain layers or materials that are "above" or "below" one another, are used merely to describe the spatial relationship between the respective components. The upper layer or component "above" the other component need not always remain vertically above the core or component, and the lower layer or component "below" the other component need not always remain vertically below the core or component. Indeed, embodiments of the present invention include various configurations whereby the core may be folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "fibrous material" denotes any fibrous material that may be used in an absorbent garment, including, without limitation, various hardwood and softwood fluff pulps, tissues, cottons, tows including cellulose acetate and any other fibrous materials described herein. "Fibrous material" used in the context of the present invention is not intended to limit the invention to any particular type of fibrous material.

Absorbent garments and diapers may have a number of different constructions. In each of these constructions it is generally the case that an absorbent core is disposed between a liquid pervious, body-facing top sheet, and a liquid impervious, exterior back sheet. In some cases, one or both of the top sheet and back sheet may be shaped to form a pant-like garment. In other cases, the top sheet, back sheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure. For clarity, the present invention is described herein only with reference to a training pant-type garment in which the top sheet, back sheet and absorbent core are assembled onto a chassis layer that forms a pant-like garment, although the invention may be used with other constructions. Although the various embodiments of the invention are described in the context of a training pant, it is readily apparent and understood that this is not intended to limit the invention. The present invention may be used with any other absorbent garment having standing leg gathers incorporated therein.

Although the absorbent core of an absorbent garment typically is capable of absorbing and storing a relatively large quantity of body exudates, insults or voids of excessive quantities of urine and/or body waste generates fluid more rapidly than the core can absorb in the given time period. It is not uncommon for a "pool" of fluid to exist on the top sheet as the absorbent core attempts to absorb the fluid as fast as possible. Accordingly, many absorbent garments include standing leg gathers to minimize or prevent leakage of any "pooled" or excess body exudates. The containment capabilities of these standing leg gathers typically are enhanced by including elastics along the length of the standing leg gather to provide an elastic contractile force which further constricts the standing leg gather against the leg of the wearer, further reducing the potential for leakage of unabsorbed body exudates.

Figure 8:
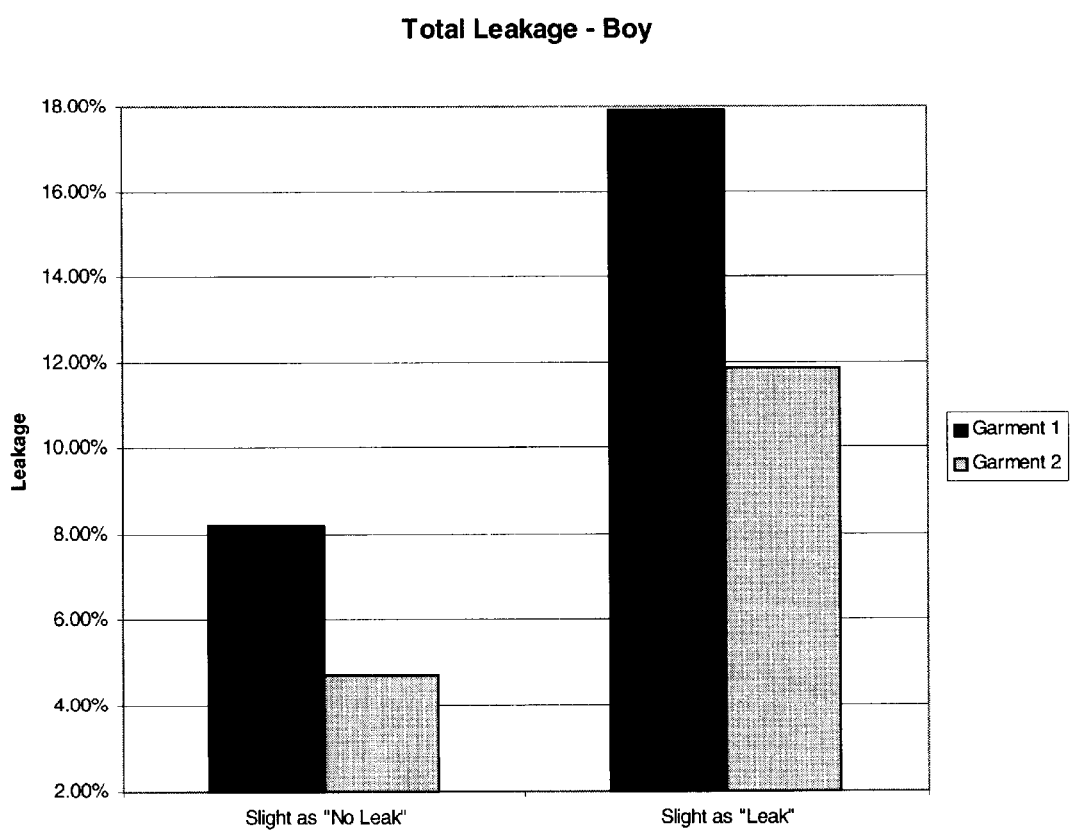
FIG. 8 is a graph showing total leakage for boys for an inventive garment and a comparative garment.
Figure 9:
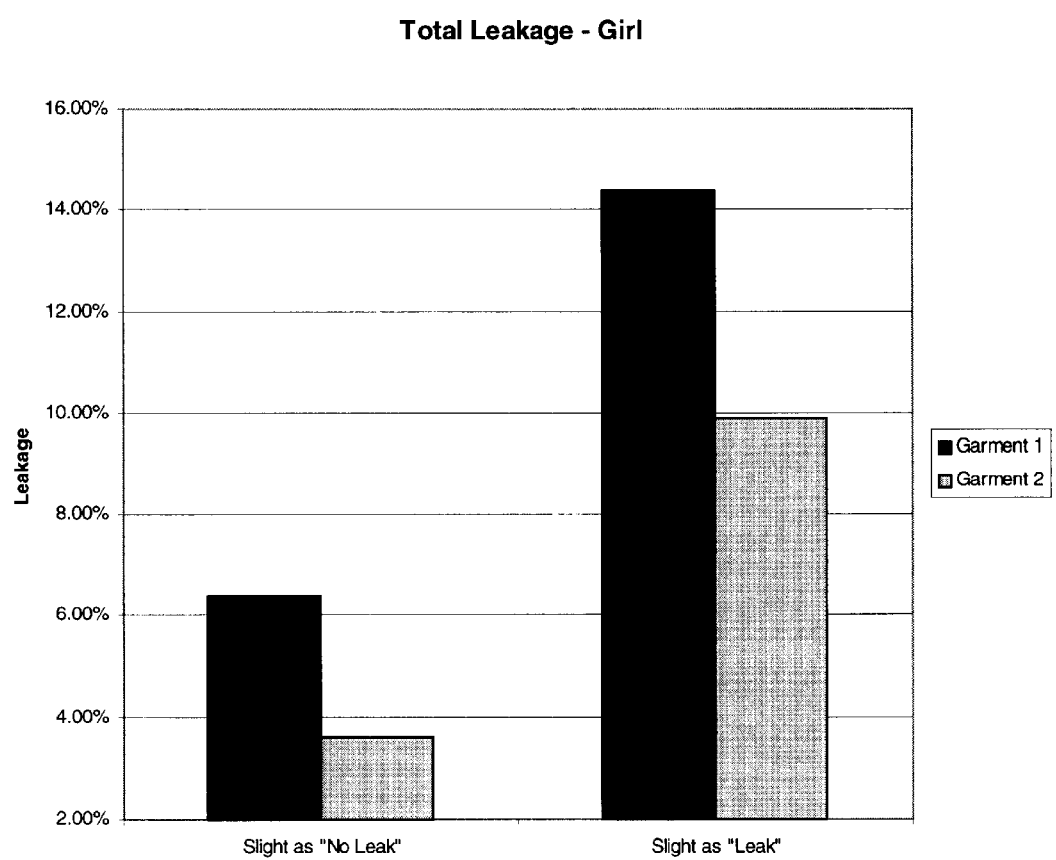
FIG. 9 is a graph showing total leakage for girls for an inventive garment and a comparative garment.

The applicants have found that the ability of a standing leg gather to prevent or minimize leakage is related to the height of the standing leg gather and the elastic contractile force provided by the one or more gather elastics within the standing leg gather. With reference to FIGS. 8 and 9, the total proportion of leaks for infant boys and girls wearing a conventional diaper (Garment 1) and a diaper in accordance with the present invention (Garment 2) are compared. Garment 1 and Garment 2 differ in only two aspects: different standing leg gather constructions and differing methods of applying adhesive to the various elastics of the diapers. For the standing leg gathers, the difference between the two is primarily in an increased height and the increased number and type of leg gather elastics (and hence an increase in the elastic contractile force) of the standing leg gather (Garment 2) in accordance with the present invention when compared to the known standing leg gather (Garment 1). Although the different method of application of adhesive used in Garment 2 generally is advantageous compared to previous methods of applying adhesive, the inventors believe that this method has no significant advantage for the purposes of leak containment.

In each of FIGS. 8 and 9, two different leak proportions are shown: "Slight as 'No Leak,'" and "Slight as 'Leak.'" In the first leak proportion, "Slight as 'No Leak,'" slight leakage is declared insufficient to be considered an actual leak, and therefore slight leaks are omitted from the first leak proportion. However, for the second leak proportion, "Slight as 'Leak,'" slight leakage is considered to be sufficient to count as an actual leak, and, therefore, they are included as leaks.

As revealed in FIGS. 8 and 9, Garment 2 (an embodiment of the present invention) exhibited far fewer occurrences of leakage than Garment 1. To illustrate, when slight leaks are considered actual leaks, the conventional diaper had an occurrence of leakage 50.42% and 45.45% higher for boys and girls, respectively. When slight leaks are omitted from consideration, the difference is even more significant, with the conventional diaper having an occurrence of leakage 74.47% and 77.78% higher for boys and girls, respectively.

As these results demonstrate, the present invention (Garment 2) exhibits an improved leak containment ability when compared with a conventional diaper (Garment 1). Since the only material difference between these diapers that relates to leak containment is the construction of the standing leg gather of Garment 2 (i.e., an increased height and increased number of elastics/increased elastic contractile force), it follows that the combination of the improved height and the improved elastic contractile force of the standing leg gather of Garment 2 is responsible for the improved leak containment ability. In other words, the leakage containment potential of an absorbent garment can be determined in part from the height of its standing leg gathers and the elastic contractile forces generated by its gather elastics.

The ability of a standing leg gather to seal against a wearer's body (i.e., to form a gasket) for the minimization of leakage has been quantified herein as the Leg Gasketing Index (LGI). It also is possible to quantify the ability of a standing leg gather to reduce or prevent leakage by its Summation Leg Gasketing Index (SLGI), as well as its Average Leg Gasketing Index (ALGI).

The Leg Gasketing Index preferably is calculated as a product of the elastic contractile force of a standing leg gather and the height of the standing leg gather, and is represented by the equation:

$$LGI_x = F_x * H$$

where $LGI_x$ represents the Leg Gasketing Index for a particular elongation x of a section of a standing leg gather, $F_x$ represents the elastic contractile force exhibited by the section of the standing leg gather at the elongation x, and H represents the height of the section of the standing leg gather, where the height H preferably is measured from the top of the standing leg gather to where the section of the standing leg gather is joined to the top sheet. For example, if a section of a standing leg gather having a height of 40 millimeters (mm) exhibits an elastic contractile force of 0.1 kilograms (kg) at 125% elongation, then the $LGI_{125\%}$ can be calculated as 4 kg*mm (0.1 kg*40 mm).

Similarly, a summation of the LGI values at a specified elongation for a section of a standing leg gather for a number of elongation cycles can be quantified herein as the Summation Leg Gasketing Index (SLGI). The calculation of an SLGI preferably includes utilizing the following equation:

$$SLGI_x = \sum_{i=1}^{k} F_{x,i} * H$$

where $SLGI_x$ is the Summation Leg Gasketing Index for a certain elongation x of the standing leg gather section (x=1.5L or x=150% elongation, for example), k represents the number of elongation cycles performed on the standing leg gather section, $F_{x,i}$ represents the elastic contractile force exhibited by the standing leg gather section at the specified elongation x during each of the k elongation cycles, and H is the height of the standing leg gather section. For example, if a standing leg gather section having an unloaded length L of 2 inches and a height H of 40 mm is elongated from an unloaded length L of 2 inches to a length of 3.0 inches (1.5L or 150% elongation) three times (i.e., k=3) and is measured to have an elastic contractile force F for each cycle of 0.25 kg, 0.23 kg, and 0.22 kg, respectively, then the $SLGI_{1.50\%}$ can be calculated as 28 kg*mm. It will be appreciated that the SLGI value associated with a standing leg gather section for a specified elongation can be divided by the number of cycles k to determine the mean LGI value of the standing leg gather section for the specified elongation for the k cycles.

The test methods described below carry out three cycles for each elongation of leg gather section. That is, the leg gather section is stretched and relaxed three separate times, and the elastic contractile forces measured for various elongations. Carrying out the tests for three cycles more accurately reveals an elastic material's behavior in use, and it reveals the material's ability to retain its elasticity. In practical use, standing leg gathers often are stretched and relaxed a number of times during use.

An average of the LGI values for a number of different elongations of a section of a standing leg gather has been quantified herein as the Average Leg Gasketing Index (ALGI). The calculation of the ALGI preferably includes using the following equation:

$$ALGI = \sum_{j=1}^{m} F_j * H$$

where ALGI represents the Average Leg Gasketing Index for a certain standing leg gather section, m represents the number of different elongation lengths represented in the calculation of the ALGI, $F_j$ represents the elastic contractile force exhibited by the standing leg gather section at an elongation length ($j_1$=150%, $j_2$=175%, and $j_3$=195%, for example), and H represents the height of the standing leg gather section, as discussed previously. To illustrate the use of the above equation, assume that a 2 inch unloaded standing leg gather section having a height H of 40 mm is elongated to 3.0 inches (1.5L or 150%) and the elastic contractile force $F_1$ at this elongation is measured as 0.1 kg. Also assume that the standing leg gather section is further elongated to 3.5 inches (1.75L or 175%) and then to 3.9 inches (1.95L or 195%), where the elastic contractile forces $F_2=0.2$ and $F_3=0.5$, respectively, are measured. In this case, the ALGI is calculated as 32 kg*mm ((0.1 kg+0.2 kg+0.5 kg)*40 mm). As with the SLGI, the ALGI can be divided by the number m of elongation lengths measured to determine the mean LGI value for the standing leg gather over the m elongation lengths. Using the previous example, this mean LGI value over the elongation lengths of 150%, 175% and 195% can be calculated to be 10.67 kg*mm.

Additionally, a total LGI (TLGI) can be determined using the following equation:

$$TLGI = \frac{\sum_{k=1}^{p} \sum_{j=1}^{m} F_{j,k} * H}{m * p}$$

where TLGI represents the Total Leg Gasketing Index for a certain standing leg gather section, m represents the number of different elongation lengths represented in the calculation of the TLGI, p represents the number of elongation-relaxation cycles, $F_{j,k}$ represents the elastic contractile force exhibited by the standing leg gather section at an elongation length ($j_1=150\%$, $j_2=175\%$, and $j_3=195\%$, for example) for cycle k, and H represents the height of the standing leg gather section, as discussed previously. To illustrate the use of the above equation, assume that a 2 inch unloaded standing leg gather section having a height H of 40 mm is elongated to 4 inches (200%) and then relaxed back for 3 cycles (p=3), and the elastic contractile force is measured at 105%, 125%, 150%, 175%, and 195% elongation during the stretching phase of the cycle. For this example, assume that elastic contractile forces F of 0.005 kg, 0.004 kg, and 0.003 kg are measured at 105% elongation (2.1 inches) for the three cycles, elastic contractile forces of 0.025 kg, 0.024 kg, 0.023 kg are measured at 125% elongation (2.5 inches) for the three cycles, elastic contractile forces of 0.1 kg, 0.095 kg, 0.090 kg are measured at 150% elongation (3 inches) for the three cycles, forces of 0.2 kg, 0.19 kg, and 0.18 kg are measured at 175% elongation (3.5 inches) for the three cycles, and forces of 0.5 kg, 0.45 kg, 0.43 kg are measured at 195% elongation (3.9 inches) for the three cycles. In this case, the TLGI is calculated as 6.184 kg*mm.

Figure 2:
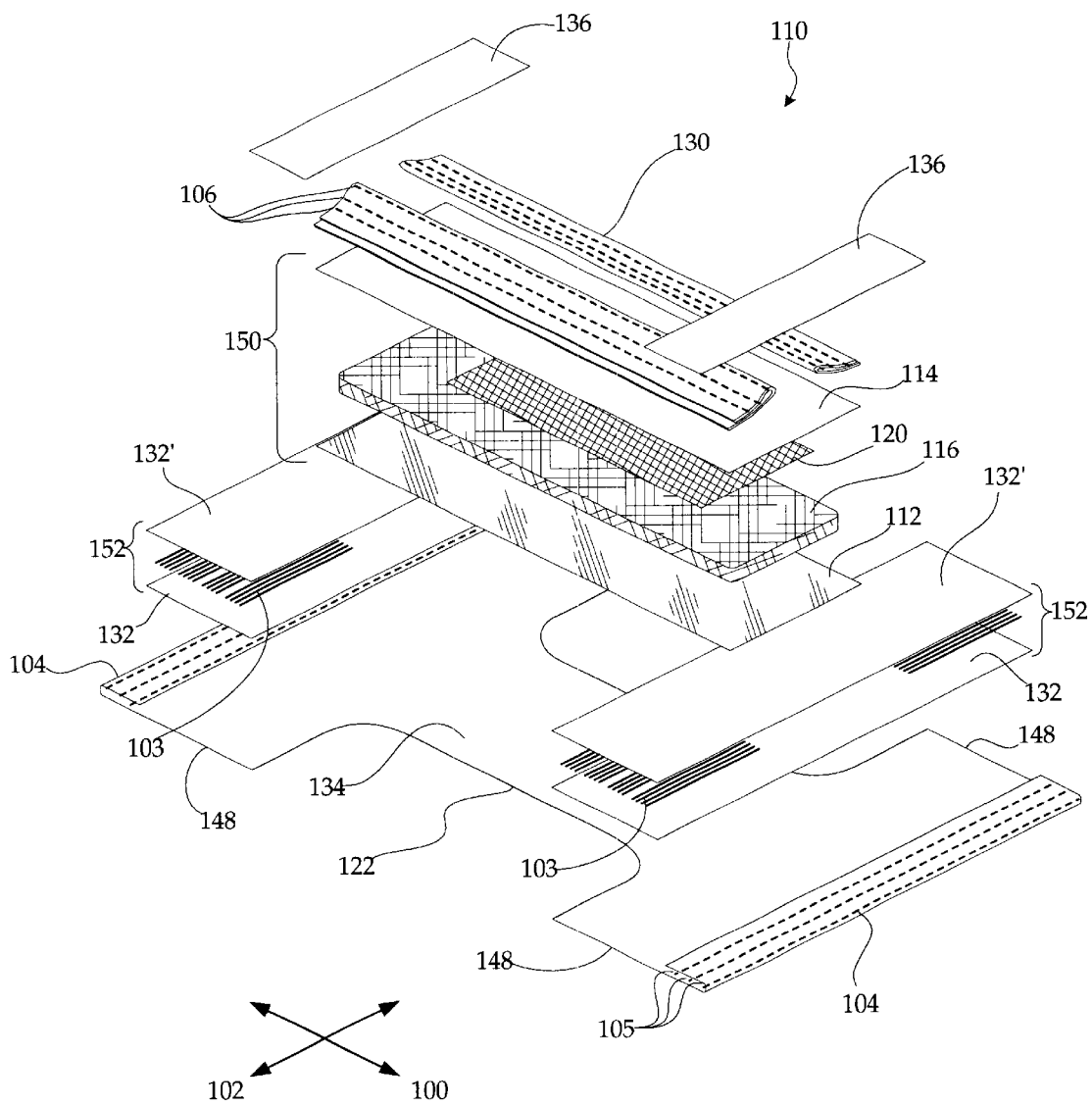
FIG. 2 is an exploded isometric view of a disposable absorbent garment in accordance with at least one embodiment of the prevent invention with the effects of the elastics removed for purposes of explanation and clarity.
Figure 3:
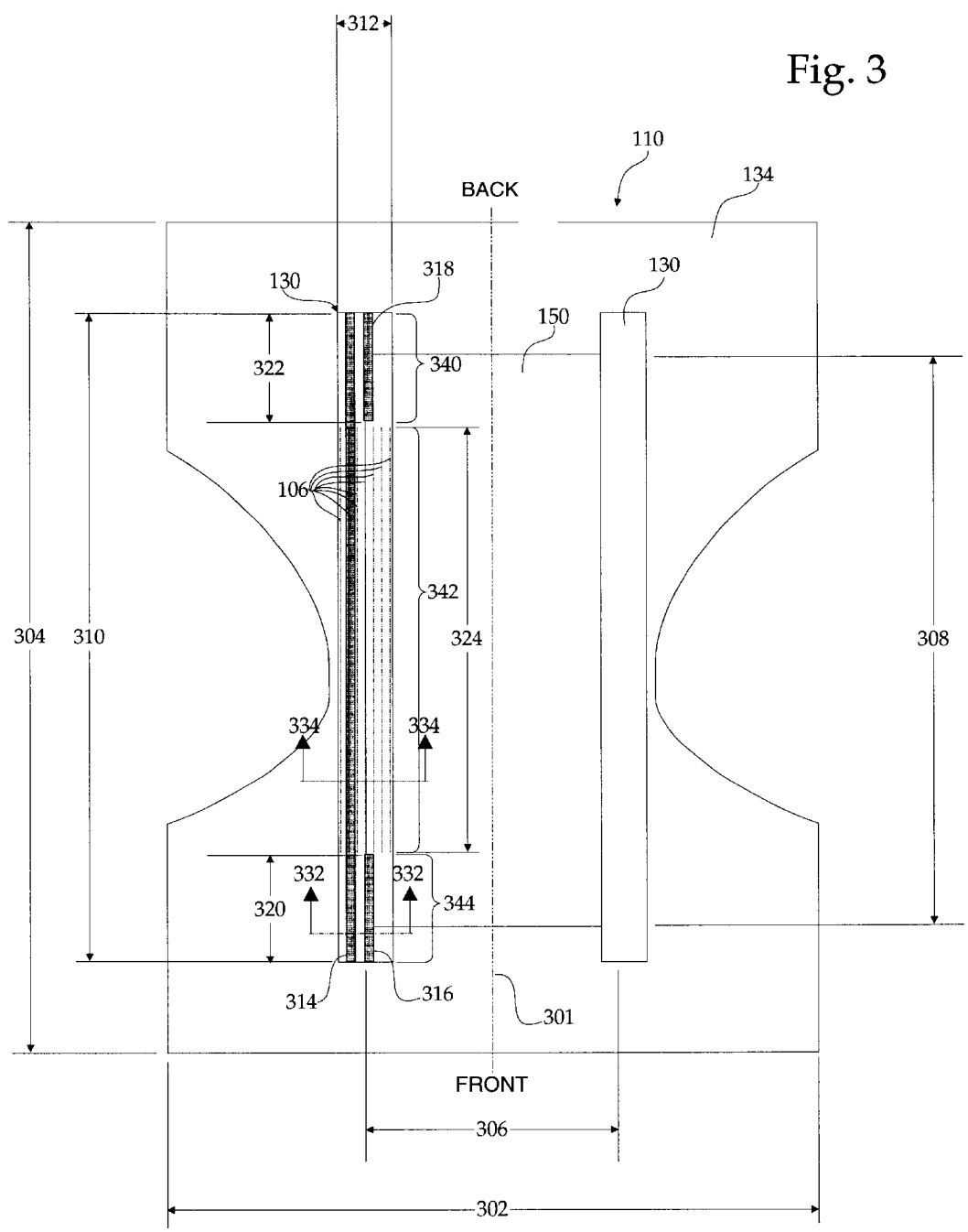
FIG. 3 is a top view of a disposable absorbent garment in accordance with at least one embodiment of the present invention.
Figure 4:
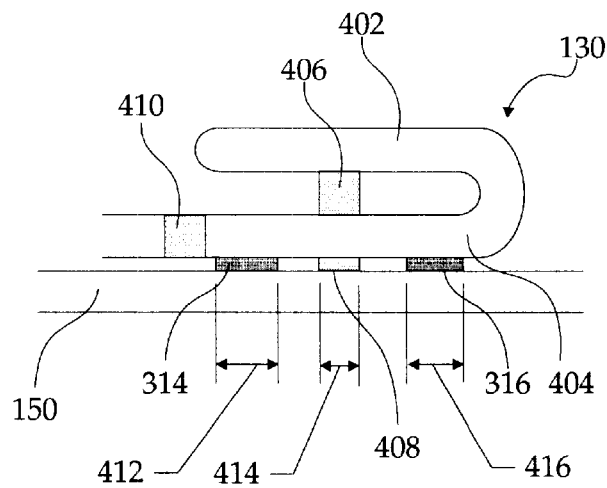
FIG. 4 is a cross-section view of an end portion of a standing leg gather taken along line 332—332 of FIG. 3 in accordance with at least one embodiment of the present invention.
Figure 5:
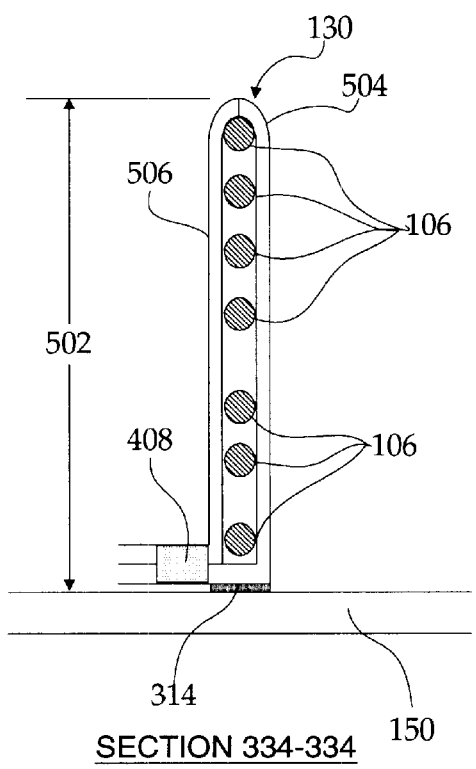
FIG. 5 is a cross-section view of a middle portion of a standing leg gather taken along line 334—334 of FIG. 3 in accordance with at least one embodiment of the present invention.

In a preferred embodiment, it has been found that a standing leg gather having an improved Leg Gasketing Index, as measured by the method provided herein, has proven beneficial when utilized in an absorbent garment as described with reference to FIGS. 1–5. FIG. 1 is a perspective view of an absorbent garment according to one embodiment of the present invention, depicted as it typically appears when being worn. FIG. 2 is an exploded isometric view of the garment of FIG. 1. FIG. 3 is a top view of the absorbent garment illustrating a particular preferred position and structure of the standing leg gathers in relation to the remainder of the absorbent garment. FIGS. 4 and 5 are cross sectional views of various sections of preferred standing leg gathers of the absorbent garment.

In the embodiment illustrated with reference to FIGS. 1–4, the garment 110 typically comprises a main chassis layer 134 that forms a pant-like garment 110 having two leg hole cutouts 122 and a pair of longitudinal ends 104. Lateral edge portions 148 join the respective ends of each leg hole cutout 122 to each longitudinal end 104. A pant-like structure may be formed by joining lateral edge portions 148 to one another to form side seams. The lateral edge portions 148 may be joined during manufacture by any mechanism known in the art or by a combination of such mechanisms. Examples of such mechanisms include: applying adhesives such as hot melt adhesives and construction adhesives, chemical or solvent bonding, stitching, heat bonding, autogenous bonding, and, preferably, ultrasonic welding. The lateral edge portions 148 also may be held proximal to one another or in an overlapping relationship during use by a fastener, such as a hook-and-loop fastener or adhesive fastener, as are well known in the art. When the lateral edge portions 148 are joined, leg hole cutouts 122 along the lateral edges of the garment 110 form leg holes, and the longitudinal ends 104 of the garment 110 form a waist encircling edge.

A core assembly 150 preferably is disposed on the interior of a chassis layer 134. The core assembly 150 may comprise an absorbent core 116 disposed between an exterior facing moisture impervious barrier film 112 or "back sheet," and a moisture pervious body-contacting inner layer 114 or "top sheet." Each of the back sheet 112, top sheet 114 and absorbent core 116 may comprise a plurality of layers of materials. In the embodiment depicted in FIGS. 1 and 2, the back sheet 112, top sheet 114, and absorbent core 116 comprise a subassembly that may be attached to the chassis layer 134. It will be appreciated that one or both of the top sheet 114 and back sheet 112 may be shaped to form the main body of a pant-like garment thereby eliminating the need for a separate chassis layer 134.

The chassis layer 134 may comprise a non-woven polyethylene or polypropylene sheet, a polyethylene film, or any other suitable garment material known in the art or hereafter discovered. All or part of the chassis layer 134 may comprise a liquid pervious or liquid impervious material or a may be zone-treated to be partially liquid pervious or impervious. The chassis layer 134 may be stretched in one or more directions during the manufacturing process, thereby reducing its elasticity in the direction of stretch.

The back sheet 112 may comprise a laminate of multiple layers of materials that have similar or different properties. The back sheet 112 preferably is made from a substantially liquid impervious material. The selection and manufacture of such materials are well known in the art, and is disclosed, for example, in U.S. Pat. No. 6,123,694 issued to Peniak et al., and U.S. Pat. No. 6,176,952 issued to Maugans et al., each of which is incorporated herein by reference in its entirety, and in a manner consistent with the present invention. In one embodiment, the back sheet 112 is made from a thin thermoplastic material, such as a pigmented polyethylene film having a thickness in the range of about 0.02 to about 0.04 mm. The back sheet 112 also may have a laminate construction comprising one or more layers of meltblown polypropylene or meltblown polyethylene, sandwiched between layers of spun-bonded material (often referred to as an "SMS" laminate). Additional layers may be added to the back sheet 112 in order to provide it with other desirable properties, such as to improve the tactile feel, or "hand." The back sheet 112 also may be entirely or partly gas pervious to allow the garment to circulate air, or "breathe."

The top sheet 114, which preferably overlays the back sheet 112, can be made from a substantially liquid pervious material to allow body exudates to penetrate into the absorbent core 116. The top sheet 114 typically comprises a carded polyester fiber with a latex binder or a spun-bonded polypropylene having continuous fibers and thermally bonded by patterned calendar rolls. The top sheet 114 may be treated over all or part of its surface to render it hydrophilic, and also may be zone-treated with a surfactant to render it hydrophilic only in certain target areas. The top sheet 114 also may be treated with skin treating ingredients, such as aloe, vitamin E, and the like, which can be accomplished by a variety of methods known in the art. The top sheet 114 also may comprise an apertured material, such as an apertured film.

In a preferred embodiment of the present invention, one or more of the top sheet 114, back sheet 112 and chassis layer 134 may comprise a laminate of several layers of material, which may have different physical properties. In another embodiment, one or more of the top sheet 114, back sheet 112 and chassis layer 134 may comprise several pieces of material, which may have dissimilar physical properties, joined at or near their edges to form a multi-paneled sheet. Such an embodiment is disclosed, for example, in U.S. Pat. No. 5,275,590 issued to Huffman et al., which is incorporated herein by reference in its entirety, and in a manner consistent with the present invention.

In a preferred embodiment of the invention, the top sheet 114 and chassis layer 134 comprise non-woven materials and the back sheet 112 comprises a film material. The top sheet 114, back sheet 112 and chassis layer 134 also may be made, however, from any other suitable material. In various embodiments, one or more of the top sheet 114, back sheet 112 and chassis layer 134 may be selected to provide particular benefits to the garment 110. For example, they may be selected to provide a good tactile impression, or "hand," a comfortable fit, or gas permeability to improve the breathability of the garment 110.

The absorbent core 116 may be made from any absorbent material or materials known in the art. It is preferred that the absorbent core 116 comprise a fibrous web having particles of superabsorbent polymer (SAP) distributed therein. In one embodiment of the invention, the absorbent core 116 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 116 comprises a combination of a porous fibrous web and super absorbent particles. Absorbent cores are known in the art and are disclosed in, for example, U.S. Pat. Nos. 5,281,207 and 6,068,620 issued to Chmielewski et al., U.S. Pat. No. 4,610,678 issued to Weisman et. al., U.S. Pat. No. 5,137,537 issued to Herron et. al., and U.S. Pat. No. 5,147,345 issued to Young et. al., which are incorporated herein by reference in their entirety.

Other suitable absorbent core materials include "tow-based" low-density cores having a relatively high concentration of SAP. Tow-based cores generally include absorbent cores having a fibrous web of relatively continuous strands that are typically provided in the form of a compact fibrous tow that has been "opened" or "bloomed" into a relatively low density, cotton-like material. Such materials may be desirable for creating absorbent cores 116 having relatively low density fibrous webs and high SAP concentrations because they have the machine direction strength (provided by the relatively long fibers) to be conveyed by machinery without breaking apart, as may occur when conventional fluff pulp-based cores are provided at very low densities.

Tow-based absorbent cores 116 and garments 110 produced there from are disclosed in, for example, U.S. Pat. No. 6,068,620 to Chmielewski and U.S. Statutory Invention Registration No. H1,565 to Brodof et al., which are both incorporated by reference herein in their entirety. Exemplary materials for such a core include cellulose acetate fibers (which are preferred), rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, blends of the foregoing materials, and the like. It has been found that these fibrous materials maintain high SAP efficiencies when the SAP concentration is in the range of about 30–95%, more preferably about 60–90%, and most preferably about 75–85%.

Any superabsorbent polymer (SAP) now known or later discovered may be used to supplement or provide the absorbent capacity of the absorbent core 116, whether the core be of conventional design or a tow-based core, so long as it is capable of absorbing liquids. Useful SAP materials are those that generally are water-insoluble but water-swellable polymeric substances capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Also included are water swellable polymers of water soluble acrylic or vinyl monomers crosslinked with a polyfunctional reactant. Such modified polymers also may be cross-linked to reduce their water-solubility, and such cross-linked SAPs have been found to provide superior performance in some absorbent cores. A more detailed recitation of superabsorbent polymers is found in U.S. Pat. No. 4,990,541 to Nielsen, the disclosure of which is incorporated herein by reference in its entirety. Mixtures and blends of SAPs also may be used.

Commercially available SAPs include a starch modified superabsorbent polymer available under the trade name SANWET® from Hoechst Celanese Corporation, Portsmouth, Va. SANWET® is a starch grafted polyacrylate sodium salt. Other commercially available SAPs include a superabsorbent derived from polypropenoic acid, available under the trade name DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; FAVOR manufactured by Stockhausen Inc; HYSORB from BASF Atkienqesellshaft, Ludwigshafen, Germany; DIAWET, available from Mitsubishi Chemical Company, Japan, FLOSORB, available from SNF Floerger, 41, rue Jean-Huss, 42028 Saint-Etienne Cedex 1-FRANCE; and AQUALIC, available from Nippon Shokubai, 4-1-1, Koraibashi, Chuo-ku, Osaka, JAPAN.

The SAP may be provided in any particle size, and suitable particle sizes vary greatly depending on the ultimate properties desired. For example, a fine particulate rather than a coarse particulate may be used in the invention, and preferably a fine particulate that passes through an about 200 mesh screen may be used.

The absorbent core 116 may be surrounded by a liquid pervious tissue over-wrap (not shown), or other material, which may be treated to be hydrophobic or hydrophilic, or to have other properties. The absorbent core 116, and any tissue wrap enclosing it, may be folded, crimped, thermally bonded, or otherwise manipulated to provide additional benefits. It is envisioned that a variety of folding patterns may be employed to provide additional fluid handling capabilities. For example, the absorbent core 116 may be folded into a U shape, a C shape, a G shape, a Z shape, or other shapes, as viewed along the longitudinal axis 100, to provide fluid handling channels, multiple layers of absorbent material, or other benefits. Folded absorbent cores are discussed, for example, in U.S. Pat. No. 6,068,620.

The absorbent core 116 generally is elongated along the longitudinal axis 100 of the garment, and may extend along either or both of the lateral axis 102 and the longitudinal axis 100 to the outer perimeter of the garment. In the embodiment depicted in FIGS. 1 and 2, the absorbent core 116 is substantially rectangular in shape, however, it also may have rounded ends or other shapes, such as an "I" shape or a "T" shape. The absorbent core 116 also may have channels, grooves or pockets, and may have a varying thickness. In an embodiment having a channeled or pocketed absorbent core 116, such channels or pockets may be substantially vacant, or may be filled with additional SAP or additional supplemental absorbent cores having similar or different properties than the absorbent core 116.

The various parts of the garment 110 preferably are operatively associated with one another in such a manner that the garment will maintain its desired structure during use. The parts may be operatively associated with one another by a variety of methods known in the art, including, but not limited to: using adhesives such as hot melt adhesives and construction adhesives, chemical or solvent bonding, ultrasonic welding, stitching, heat bonding, autogenous bonding, or any other method of affixation known or hereafter discovered. U.S. Pat. No. 4,919,738 issued to Ball et. al. discloses a method of autogenous bonding, and its disclosure is herein incorporated by reference in its entirety in a manner consistent with the invention. All of the parts may be joined to each adjacent part, but some parts may not be joined to others. In one embodiment, the top sheet 114 and back sheet 112 are bonded to one another around their perimeter regions, thereby encasing and holding the absorbent core 116 in place without having to join directly the absorbent core 116 to any parts of the garment 110. The top sheet 114 or back sheet 112 also may be operatively associated with the absorbent core 116. As understood herein, the term "operatively associated" includes directly joining one part to another, indirectly joining parts together through one or more intermediary parts, whether those intermediary parts are described herein or not, joining parts in such a manner that un-joined parts are captured or held in their proper place, and any other suitable joining means that maintains the structural integrity of the garment 110 for the duration of its use.

The core assembly 150 may comprise additional layers 120 of material that may reduce rewet of the top sheet 114, reduce strikethrough times or otherwise improve the absorbency, dryness and other properties of the garment 110. Examples of the one or more additional layers 120 include any layer selected from a fluid acquisition layer, a distribution layer, an additional fibrous layer optionally containing SAP, a wicking layer, a storage layer, or combinations and fragments of these layers. Such layers may be provided to assist with transferring fluids to the absorbent core 116, handling fluid surges, preventing rewet, containing absorbent material, improving core stability, or for other purposes. Skilled artisans are familiar with the various additional layers that may be included in an absorbent article, and the present invention is not intended on being limited to any particular type of materials used for those layers. Rather, the invention encompasses all types of wicking layers, all types of distribution layers, etc., to the extent that type of layer is utilized.

The core assembly 150 may be attached to the chassis layer 134 by any means known in the art, such as by ultrasonic bonding or by the use of lines of hot melt adhesive. The bond between the core assembly 150 and the chassis layer 134 may be reinforced by laterally-extending end strips 136 that are applied over the longitudinal ends of the core assembly 150 and bonded to the underlying structure of the garment 110. The end strips 136 also may hold the ends of the standing leg gathers 130 so that the standing leg gathers 130 (described below) face inward or outward. Such end strips 136 preferably comprise a fluid pervious nonwoven material, but may be fluid impervious or a material other than a non-woven material. Such materials are known in the art. The end strips 136 also may help prevent the longitudinal flow of exudates past the ends of the core assembly 150, particularly if the edges of the non-woven strips overlying the core assembly 150 are left un-bonded so that they form pockets to hold exudates.

Waist elastics 105 and tummy elastics 103 may be incorporated into the garment 110 to contract the garment 110 about the wearer's abdomen. Such elastics are typically stretched as they are joined to the garment 110 so that the contraction of the elastics causes the garment 110 to contract about the wearer. The elastics also may be applied in an unstretched state and then mechanically stretched to create an elasticized region in the garment (often called a zero-strain laminate). The elastics also may be applied in an inelastic state and then heat activated to cause them to become elasticized. The elastics 103, 105, and 106 may be made from natural or synthetic rubber, elastomers, LYCRA® elastomer (available from E. I. DuPont de Nemours and Company, a business having offices in Wilmington, Del.), polyurethane, heat shrinkable polymer ribbons, or any other suitable elastic material or composite. Such materials are known in the art.

In a preferred embodiment, the waist elastics 105 are located proximal to one or both longitudinal ends 104 of the chassis layer 134, and are thereby located along the waist encircling edge of the fully assembled garment 110. In such an embodiment, the waist elastics 105 may be located on one side of the chassis layer 134, within a fold in the chassis layer 134 (as shown in FIG. 2), or otherwise fixed in the proximity of the longitudinal ends 104. U.S. Pat. No. 4,515,595 issued to Kievit et. al. and U.S. Pat. No. 4,816,025 issued to Foreman illustrate other embodiments of elasticized waist features of absorbent garments, and are hereby incorporated by reference in their entirety and in a manner consistent with the present invention.

Tummy elastics 103 also may be disposed in the garment 110 between the longitudinal ends 104 and the leg opening cutouts 122 to thereby be positioned across the wearer's stomach. The tummy elastics 103 may be attached directly to the chassis layer 134 or may be disposed between a pair of carrier layers 132, 132' to form tummy elastic assemblies 152 that are attached to the chassis layer 134. The tummy elastics 103 may be located on the interior or exterior side of the chassis layer 134, and may be covered by additional layers of material. In a preferred embodiment, the tummy elastics 103 are affixed between a pair of carrier layers 132, 132'. The carrier layers 132, 132' preferably comprise nonwoven materials, but may be made of any suitable material, and may be liquid pervious or liquid impervious. The carrier layers 132, 132' are preferably gas pervious to allow the garment 110 to "breathe."

In one embodiment, the tummy elastics 103 may extend across the entire width of the garment 110. In a preferred embodiment, shown in FIGS. 1 and 2, the tummy elastics 103 extend across the lateral sides of the garment 110, but not across the portion of the garment 110 overlying the absorbent core 116. Such a preferred embodiment may provide improved fit and comfort and improve the garment's appearance. U.S. Pat. No. 5,449,353 issued to Watanabe et. al. and U.S. Pat. No. 5,749,865 issued to Yamamoto et al. illustrate other embodiments of elasticized waist features of absorbent garments, and are incorporated herein by reference in their entirety, and in a manner consistent with the present invention.

The elastics 103, 105, 106 or any other elastics may be joined to the garment 110 by the use of a flexible adhesive or other suitable joining method. Suitable adhesives include HL-1258 by H. B. Fuller Company of St. Paul, Minn.; Findley 2031 and H2587-01 by Ato Findley Inc. of Wauwatosa, Wis.; and NS34-5665 by National Starch Co of Bridgewater, N.J. Adhesives that may be used to secure elastic elements to the absorbent garment include 34-578A by National Starch Co. of Bridgewater, N.J. In a preferred embodiment of the invention, the adhesive utilized includes HL 1486UZP, which is available from H. B. Fuller Company of St. Paul, Minn. This and other methods for attaching elastics to absorbent garments are known in the art.

As noted previously, it often is desirable for an absorbent garment to contract around various parts of the wearer's body to provide improved comfort and exudate containment. In a preferred embodiment of the present invention depicted in FIGS. 1–5, the garment 110 further comprises at least one standing leg gather 130, and preferably at least 2 standing leg gathers 130, for improving the ability of the garment 110 to contain body exudates. The standing leg gathers 130 may be formed by incorporating a plurality of gather elastics 106 into folds in the top sheet 114, or preferably may be provided as separate standing leg gather assemblies that are attached to the garment 110 near the leg hole cutouts 122. The gather elastics 106 cause the standing leg gathers 130 to rise above the interior surface of the garment 110, thereby forming vertical curtains of material that help contain exudates. The standing leg gathers 130 may be liquid pervious or liquid impervious, and more than one pair of opposing standing leg gathers 130 may be provided. For ease of discussion, the standing leg gathers 130 will be described subsequently as secured to the core assembly 150, such as being secured to the top sheet 114. However, the standing leg gathers 130 may be secured to or disposed on any other suitable part of the garment so long as they are positioned in a manner that they block or impede the passage of fluids and other exudates.

Additional elastics (not shown) also may be incorporated into the chassis layer 134, top sheet 114 or back sheet 112 adjacent the leg hole cutouts 122 to form non-standing leg gathers, as is known in the art. Non-standing leg gathers contract the garment 110 around the wearer's legs and body to prevent leakage. U.S. Pat. Nos. 3,860,003 and 4,081,301 issued to Buell, U.S. Pat. No. 4,695,278 issued to Lawson, U.S. Pat. No. 4,808,177 issued to Des Marais, U.S. Pat. No. 4,795,454 issued to Dragoo, and U.S. Pat. No. 4,938,755 issued to Foreman illustrate other embodiments of leg cuffs and gathers in absorbent garments, and the disclosures of these patents are hereby incorporated by reference in their entirety, and in a manner consistent with the present invention.

FIGS. 3–5 illustrate the standing leg gathers 130 and their relation to the remainder of the garment 110 in greater detail. In the embodiment depicted in FIG. 3, the chassis layer 134 of garment 110 preferably has a width (dimension 302) between about 260 mm and about 750 mm and a length (dimension 304) between about 360 and about 1000 mm. The core assembly 150 of the garment 110 preferably has a width (dimension 306) of about 100 mm and a length (dimension 308) between about 300 mm and about 700 mm.

A pair of standing leg gathers 130 preferably are provided on opposing sides of the core assembly 150, where the two standing leg gathers 130 are positioned longitudinally along the length of the garment 110. The two standing leg gathers 130 preferably have a length (dimension 310) of about 450 mm to about 650 mm and a width (dimension 312) of about 15 mm to about 50 mm, preferably about 27.5 mm, when "folded" as discussed with reference to FIG. 4. Although the standing leg gathers 130 are illustrated as having a length (dimension 310) less than the length (dimension 304) of the chassis layer 134, it will be appreciated that the standing leg gathers 130 that are disposed along the entire length of the chassis layer 134 can be implemented in accordance with the present invention.

The standing leg gathers 130, in one embodiment, are secured to the core assembly 150 at continuous bond region 314, which is disposed along a substantial portion of their length (dimension 310). The standing leg gathers 130 may be attached to the core assembly 150 along continuous bond region 314 using any mechanism known in the art, such as ultrasonic welding, thermal bonding, stitching, or the use of hot melt adhesive or a combination of one or more of these mechanisms. The lengths (dimensions 320, 322) of the bond regions 316, 318 preferably are between about 30 mm and 80 mm. Skilled artisans will recognize that the length (dimension 320) of bond region 316 and the length (dimension 322) of bond region 318 may be the same or different.

In addition to securing the standing leg gathers 130 to the core assembly 150 along continuous bond region 314, in a preferred embodiment, the end portions 340, 344 of the standing leg gathers 130 are further secured at partial bond regions 316, 318 to core assembly 150, where the partial bond regions 316, 318 are disposed along a substantial portion of the length of the respective end portions 340, 344, and are located between the continuous bond region 314 and the longitudinal centerline 301. Additionally, an end bond preferably secures each of end portions 340, 344 so that the end portions are "folded over" onto themselves, as shown in greater detail in FIG. 4. However, as the middle portion 342 preferably is unsecured to itself by any such bond, the middle portion 342 is not inhibited from "standing" vertically when the garment 110 is in use. The end bonds, omitted from FIG. 3 for ease of illustration, may incorporate any known bonding method or material, such as ultrasonic welding or chemical adhesives. Those skilled in the art can develop mechanisms and/or materials to secure the standing leg gather 130 with or without the end bonds, using the guidelines provided herein.

As noted previously, the leak containment ability of a leg gather is based on, in part, the elastic contractile force exhibited by the leg gather. Accordingly, the standing leg gathers 130 include a plurality of gather elastics 106 to provide an elastic contractile force along a substantial portion of the longitudinal extent (i.e., length) of the standing leg gathers 130. In a preferred embodiment, the leg gathers 130 each include more than four, and preferably up to about seven gather elastics 106 composed of LYCRA® elastomer (available from E. I. DuPont de Nemours and Company) having a decitex (dtex) between about 400 and about 1300, preferably between about 550 and about 1200, and more preferably between about 680 and about 940 to provide a total average elastic contractile force of at least about 12.36 kg at 105% elongation and of at least about 158.7 kg at 195% elongation. As illustrated in FIG. 3, the gather elastics 106 are provided along a substantial portion (dimension 324) of the standing leg gathers 130. In a preferred embodiment, the elastics 106 are disposed in the middle portion 342 and terminate before the end portions 340, 344 since the effectiveness of the gather elastics 106 at the end portions 340, 344 typically is limited due to the bond regions 316, 318, when present. Cross-section views of the garment 110 at cross-section 332 and cross-section 334 are illustrated in FIGS. 4 and 5, respectively.

Referring now to FIG. 4, a cross-section of the end portion 344 of a standing leg gather 130 at cross-section 332 is illustrated. The following discussion applies equally to end portion 340 unless otherwise noted. The end portion 344 of the standing leg gather 130 preferably is bonded to the core assembly 150 in two bond regions, bond region 314 and bond region 316, as discussed previously. Additionally, in the embodiment depicted in FIG. 4, the upper portion 402 of the end portion 344 preferably is secured to the lower portion 404 of the end portion 344 at end bond 406, which adheres the upper portion 402 to the lower portion 404 so that the end portion 344 is "folded over." Likewise, the end bond to secure the upper portion 402 to the lower portion 404 may be extended to secure the lower portion 404 to the core assembly 150 at end bond 408. For example, the top portion 402 can be secured to the lower portion 404 and the lower portion 404 can be secured to the core assembly 150 using a single application of a thermal bonding method. Additional bond regions may be utilized to secure the upper portion 402 to the lower portion 404. In at least one embodiment, the lower end of the standing leg gather 130 can be sealed, such as by thermal bonding, at seal region 410 to provide additional structural integrity to the standing leg gather 130.

The bond region 314 preferably is between about 2 to about 20 mm wide, more preferably from about 5 mm to about 15 mm wide, and most preferably about 10 mm wide (dimension 412). Likewise, the bond region 316 preferably is between about 2 mm to about 20 mm wide, more preferably between about 5 and about 15 mm wide, and most preferably, about 10 mm wide (dimension 414), and the end bond 406 and the seal region 408 preferably are within the range of from about 2 to about 20 mm wide, more preferably from about 5 to about 15 mm wide, and most preferably about 10 mm wide. The bonding utilized at the bond regions 314, 316 preferably includes an adhesive bonding and the bonding utilized at end bonds 406, 408, and seal region 410 preferably includes utilizing a thermal or ultrasonic welding technique. However, those skilled in the art can utilize other bonding techniques to bond the standing leg gathers 130 to the core assembly 150 at bond regions 314, 316, and to secure the standing leg gather 30 to itself at the end portions 340, 344, using the guidelines provided herein.

Securing the standing leg gathers 130 to the core assembly 150 at bond regions 314, 316, 408 so that the standing leg gathers 130 are folded over at end regions 340, 344 often proves beneficial in a number of ways. By folding over the end portions 340,344 of the standing leg gathers 130, the garment 110 is more easily maneuvered during the manufacturing process, since the folded standing leg gathers 130 have a lower overall height and are less likely to snag during manufacturing. Additionally, by securing the end portions 340, 344 of the standing leg gathers 130 to the core assembly 150 in a folded position, the middle portion 342 of the standing leg gather 130 that is bonded to the core assembly 150 only at bond region 314 typically is capable of exerting an increased contractile force due to the relative immobility of its end portions 340, 342, thereby improving the fit of the standing leg gathers 130 against the wearer's leg.

FIG. 5 illustrates a cross-section of the middle portion 342 of the standing leg gather 130 at cross-section 334 where the standing leg gather 130 is secured to the core assembly 150 only at bond region 314. As illustrated, the middle portion 342 of the standing leg gather 130 typically stands substantially vertical due to the elastic contractile forces generated by the gather elastics 106. For the unfolded portion of the standing leg gather 130, the height (dimension 502) between the utmost vertical point of the substantially vertical standing leg gather 130 and the core assembly 150 preferably is from about 20 mm to about 100 mm, more preferably from about 30 mm to about 70 mm, and even more preferably from about 35 mm to about 60 mm, and most preferably is about 40 mm.

In the embodiment depicted in FIG. 5, the standing leg gather 130 includes seven gather elastics 106 disposed between sheet portions 504, 506. Sheet portions 504, 506 can comprise separate sheets of non-woven material secured together, either directly or by securing sheet portions 504, 506 to the gather elastics 106. Alternatively, the sheet portions 504, 506 can comprise a single sheet of non-woven material folded over onto itself with the gather elastics 106 disposed between the two sheet portions 504, 506 when folded.

Figure 6:
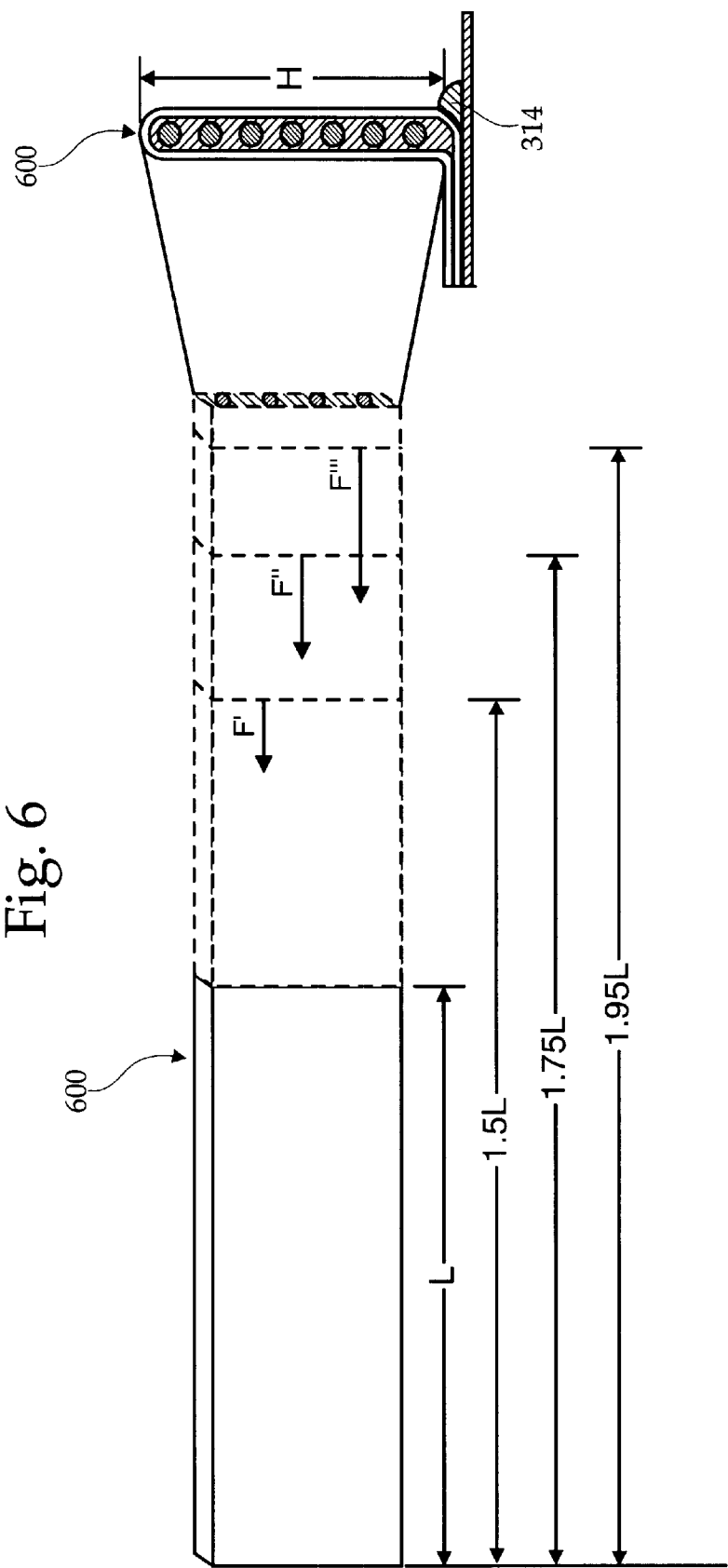
FIG. 6 is a block diagram illustrating an elastic contractile force exhibited by a section of a standing leg gather as the standing leg gather is elongated.

The gather elastics 106 can be distributed evenly between the two ends of the standing leg gather 130, thereby providing an evenly distributed elastic contractile force when the standing leg gather 130 is elongated. Alternatively, the gather elastics 106 preferably are distributed so that the elastic contractile force is unevenly distributed. For example, since the portion of the standing leg gather 130 closer to a wearer's body typically is elongated more than the portion closer to the core assembly 150, it often is beneficial to provide for more gather elastics 106 in the portion proximal to the wearer than in the portion proximal to the core assembly 150. As illustrated in FIG. 6, four of the seven gather elastics 106 are distributed along the top half of the standing leg gather 130, whereas the remaining three gather elastics 106 are distributed along the bottom half such that there is a relatively large space between the first four gather elastics 106 and the last three gather elastics 106. Skilled artisans will appreciate, however, that the standing leg gathers 130 may include any number of elastic elements distributed in any manner, so long as the material exhibits the characteristics described herein.

Figure 7:
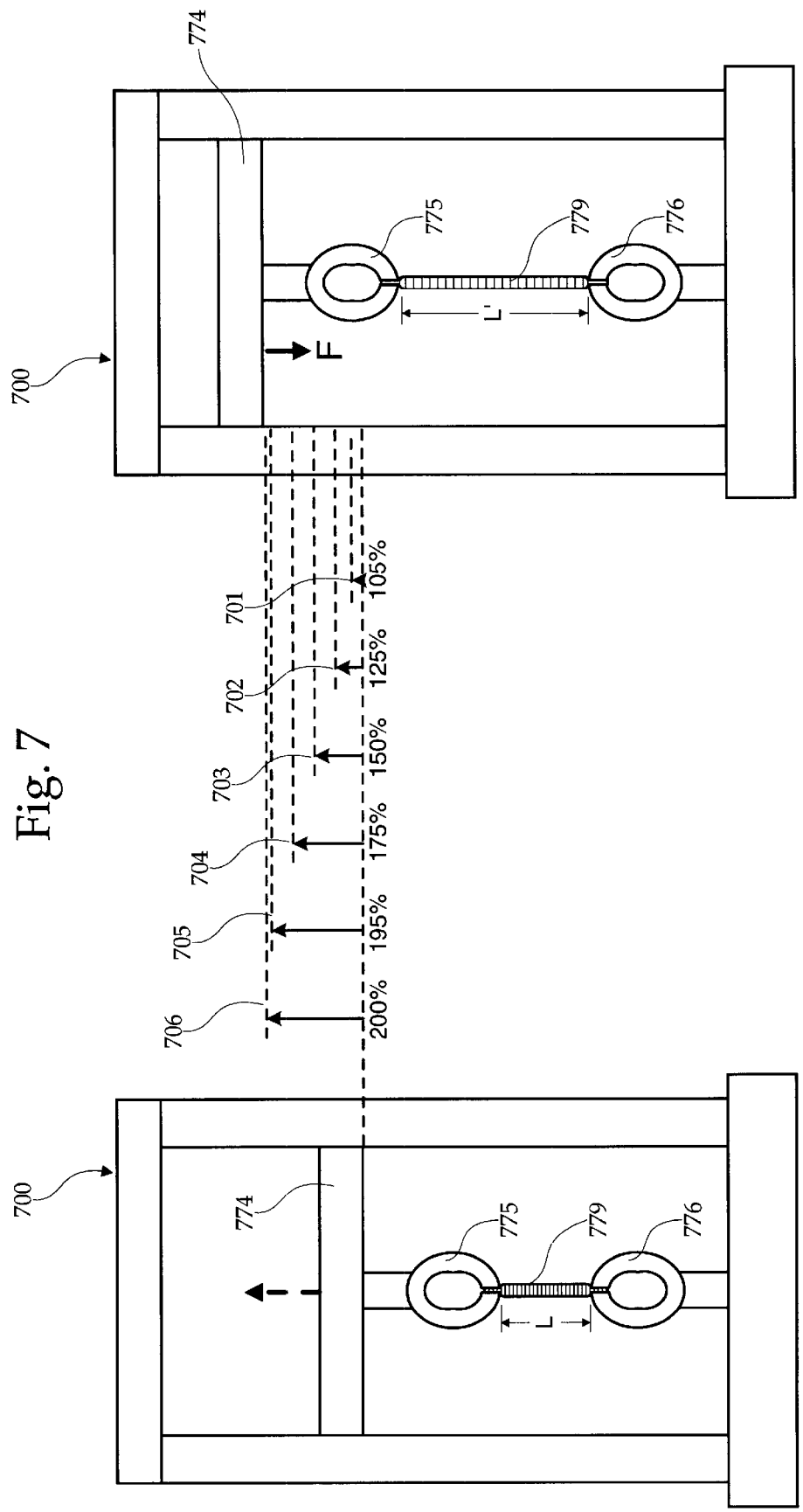
FIG. 7 is a front view of an apparatus adapted to measure an elastic contractile force exhibited by a section of a standing leg gather as it is elongated.

Referring now to FIGS. 6 and 7, an exemplary method of determining the Leg Gasketing Index (LGI), Summation LGI (SLGI), and Average LGI (ALGI) for a section of a standing leg gather is illustrated in accordance with at least one embodiment of the present invention. A longitudinal section of a standing leg gather, herein referred to as the leg gather section 600 having a unloaded, or relaxed, length L is placed in a unloaded state between the two grips of a tensile force measurement device, such as an Instron model 55R1122 available from Instron Corporation of Canton, Mass. In this example, assume the unloaded length L of the standing leg gather section 600 to be approximately 2 inches. The standing leg gather section 600 may then elongated to certain lengths, such as 3 inches (1.5*L or 150% elongation), 3.5 inches (1.75*L or 175% elongation), and/or 3.9 inches (1.95 L or 195% elongation), and the elastic contractile forces F exhibited by the standing leg gather section 600 at the certain elongated lengths can be measured by a tensile force measurement device, as described in detail subsequently.

The elastic contractile force F can then be multiplied by the height H of the leg gather section 600, where the height H preferably is measured from the top of the standing leg gather to the point where the standing leg gather 130 joins the core assembly 150 at the bond region 314 (e.g. dimension 502 in FIG. 5).

To illustrate, if a force F'=0.1 kilograms is measured at an elongation length of 3 inches (1.5L) and the height H is measured to be 40 mm, the LGI value at 3 inches (150% elongation) can be calculated to be 4.0 kg*mm ($LGI_{1.5L}$= F'*H=0.1 kg*40 mm). Likewise, if at 3.5 inches (175% elongation) the elastic contractile force F" is measured to be 0.2 kg, the corresponding LGI value can be calculated as 8.0 kg*mm ($LGI_{1.75L}$=0.2 kg*40 mm). If an elastic contractile force F'" of 0.4 kg is measured at 195% elongation (1.95L or 3.9 inches), then the corresponding LGI value can be calculated as 16 kg*mm ($LGI_{1.95L}$=0.4 kg*40 mm).

While the LGI/ALGI/SLGI value for a particular sample of a certain standing leg gather can be a relative indicator of the leak containment ability of all standing leg gathers of the same type, due to variances in the manufacturing process and in the material used to manufacture the disposable absorbent garment, it is preferable to perform a statistical analysis on a number of samples of a standing leg gather to determine a statistically significant mean LGI, ALGI, SLGI, and/or TLGI value for a standing leg gather product to determine the leg gasketing ability (i.e., the leak containment capability) of the standing leg gather.

Statistical analysis of a number of samples of standing leg gathers is particularly advantageous in determining the "overall" or average gasketing ability of a standing leg gather design or structure by minimizing the importance of those few standing leg gather samples that are not indicative of the typical properties of a standing leg gather product. A number of factors can cause those standing leg gathers having atypical values, also known in the field of statistics as "outliers".

For instance, it is known that some elastic materials may loose their elasticity as they age, i.e., they "dry out." A sample could have been selected from an absorbent garment that was manufactured long before the other absorbent garments used as sources of samples, thereby increasing the likelihood that the gather elastics of the sample have dried out and become less elastic. Likewise, variances in the manufacturing process can cause one or more deviations in a property of one or more elastic elements of an outlier sample that is not in accordance with the manufacturer's specifications. For example, the elastics of a sample in question could have been manufactured much thicker in diameter than specified by the manufacturer.

Statistical analysis of a plurality of standing leg gather products has been performed by the inventors, and it has been found that the present invention exhibits significantly higher individual and mean LGI, ALGI, and SLGI values compared to the most effective known standing leg gathers. The elastic contractile force resulting from what is believed to be a combination of the number of elastics, the material comprising the elastics, as well as the height of the standing leg gathers of various embodiments of the present invention provide a distinct advantage in minimizing the leakage of body exudates that have not yet been absorbed, as evidenced by the significantly higher LGI, ALGI and SLGI values of the present invention compared to those of known standing leg gathers. The test methods, as well as the results of these tests on a variety of standing leg gathers, are discussed in more detail below in the examples.

The present invention also relates to a method of making an absorbent garment that includes providing a top sheet material, a back sheet material, and an absorbent core to a garment forming station, and then disposing the absorbent core between the top sheet material and the back sheet material. The method also includes disposing on the top sheet material at least one longitudinally extending, elasticized standing leg gather laterally from a longitudinal centerline of the top sheet material, whereby the at least one standing leg gather includes at least one elastic element for distributing elastic contractile forces. Any and all of the above standing leg gathers with their attendant physical properties can be used in the method of the invention, including without limitation, those leg gathers having the mean Total Leg Gasketing Indices described above.

EXAMPLES

The test method utilized to determine and compare the LGI, ALGI, and SLGI of the embodiments of the present invention with those of known standing leg gathers is discussed below with reference to FIG. 7. Although a specific test method is discussed herein, those skilled in the art can develop alternate testing methods to determine the mean LGI, ALGI, and/or SLGI values for one or more standing leg gather products, using the guidelines provided herein.

The purpose of the following test method is to determine the mean LGI, mean ALGI, and mean SLGI of a number of standing leg gathers produced by a variety of absorbent garment manufactures and of two implementations of the present invention. The tests enable one to compare the test results and reveal that the present invention exhibits mean LGI, ALGI, and SLGI values significantly higher than the corresponding values of presently available standing leg gathers. The present invention, therefore, exhibits substantially improved leak containment properties when compared to known standing leg gathers.

Sample Preparation

In the test described herein, the LGI, SLGI, and ALGI values were determined for seven different standing leg gather (LG) constructions, designated LG 1 through LG 7. LG 1 and LG 2 are embodiments of the present invention and LGs 3–7 are known standing leg gathers obtained from commercially available products.

A detailed description of each of LG 1–7 follows:

LG 1: One embodiment of the present invention comprising seven strands of 940
dtex LYCRA® disposed between two non-woven sheets.

LG 2: Another embodiment of the present invention comprising seven strands of 680 dtex LYCRA® disposed between two non-woven sheets.

LG 3: A known standing leg gather implemented in absorbable garments available from Proctor & Gamble under the trade designation PAMPERS® EASY UPS®.

LG 4: A known standing leg gather implemented in absorbable garments available from Paragon Trade Brands, Norcross Ga., under the trade designation TP-99 Globe.

LG 5: A known standing leg gather implemented in absorbable garments available from Paragon Trade Brands, Norcross, Ga. under the trade designation TP-99 Lycra.

LG 6: A known standing leg gather implemented in absorbable garments available from Kimberly-Clark Corporation under the trade designation HUGGIES® PULL-UPS®.

LG 7: A known standing leg gather implemented in absorbable garments available from Kimberly-Clark Corporation under the trade designation Comforts, private label brand for Kroger.

Preparation of Equipment

An Instron 55R1122 was turned on and allowed to warm up for about 15 minutes (A front view of the Instron 55R112 is illustrated in FIG. 7 as Instron 700). The Instron 55R1122 was calibrated using the 1000 g calibration weight. The initial gauge length (L) was set to 50.8 mm (about 2 inches). The initial speed of the cross-arm 774 was set to 304.8 mm/minute (about 12 inches/min).

For each sample standing leg gather, the height H of the standing leg gather was measured and recorded to the closest 1 mm, where the height H was measured from top edge of the standing leg gather to where the standing leg gather was bonded to the core assembly, as discussed previously with reference to FIG. 6. Each sample standing leg gather was removed, using scissors, from its respective absorbent garment, taking care to ensure that each sample standing leg gather was removed as close as possible to region where the standing leg gather and the core assembly were joined.

Test Method

Sample standing leg gathers in a relaxed state were inserted longitudinally into the grips 775, 776 of the Instron apparatus. The center of the sample standing leg gathers were located between grip 775 and grip 776 (i.e., collocated with the initial gauge length L). The section of the sample standing leg gathers between the grip 775 and the grip 776 is referred to herein as the test section 779. The initial length of the test section 779 in an unloaded, or relaxed, state between the grips 775, 776 is herein referred to as the "unloaded length" and is equivalent to the initial distance between grips 775, 776 (about 50.8 mm or 2 inches).

The test section 779 of the sample standing leg gather was elongated to L'=200% (about 101.6 mm or 4 inches) of the unloaded length L. During the elongation of the test section 779, the force load exerted by the test section of the sample standing leg gather was measured (using the Instron 55R1122) and recorded during elongation at 105% elongation, 125% elongation, 150% elongation, 175% elongation, and 195% elongation (elongation points 701–706, respectively). It will be appreciated that the force load F measured by the Instron 700 represents the elastic contractile force of the test section 779 of the sample standing leg gather. Once an elongation of 200% (101.6 mm or 4 inches, elongation point 61) of the unloaded length L was achieved, the sample was held in this elongated state for 30 seconds.

The test section 779 of the standing leg gather sample then was relaxed back to the unloaded length (50.8 mm) at a rate of 304.8 mm/min and the force loads were measured and recorded at each of the respective elongations. The force loads used in calculating the LGI, ALGI, and SLGI values herein were those measured during the stretching phase, and not the relaxing phase. The test section 779 of the standing leg gather sample then was held in the unloaded state for 60 seconds. The sample then was stretched, held, and relaxed again for two more cycles for a total of three cycles. Each standing leg gather sample was subjected to this test method, and as reported in the tables below, ten (10) samples of each of each leg gather were subjected to the test method, and the average values are compared herein to provide a statistically adequate comparison.

The force loads at different elongations and during different cycles (representative of the elastic contractile force F of the corresponding test section 779) can be determined (step 3) from a printout from the printer of the Instron 55R1122, which can be a graph or a table of measurements. Likewise, the force load values resulting from the test of the sample standing leg gathers can be provided to a computer or other information processing machine for analysis.

Test Results

Tables 1–9 reveal the results of the test described above. Tables 1–7 depict the measured elastic contractile forces recorded for 3 cycles of elongation, measured at 105%, 125%, 150%, 175%, and 195% elongation, for LGs 1–7, respectively. Table 8 depicts a comparison between the mean LGI/SLGI/TLGI values of the present invention (LGs 1, 2) and the mean LGI/SLGI/TLGI values of known standing leg gathers (LGs 3–7), as determined from Tables 1–7. Similarly, Table 9 illustrates a comparison between the total/partial ALGI of the present invention and the total/partial ALGI of the known standing leg gathers, as determined from Tables 1–7.

TABLE 1

| Sample | ULG 1 | Height (mm) | 42 | |
|---|---|---|---|---|
| | Cycle 1 | Cycle 2 | Cycle 3 | SLGI |
| | Elongation: 105% | F (g) | | |
| 1 | 43.34 | 25.63 | 22.86 | 3.857 |
| 2 | 40.20 | 23.91 | 21.61 | 3.600 |
| 3 | 35.90 | 21.72 | 19.82 | 3.252 |
| 4 | 36.96 | 22.87 | 20.71 | 3.383 |
| 5 | 40.12 | 22.35 | 21.02 | 3.507 |
| 6 | 38.28 | 21.90 | 19.88 | 3.363 |
| 7 | 41.04 | 24.82 | 22.27 | 3.701 |
| 8 | 36.26 | 15.89 | 13.97 | 2.777 |
| 9 | 29.78 | 14.26 | 12.83 | 2.389 |
| 10 | 35.36 | 16.13 | 13.64 | 2.735 |
| Avg. LGI[1]: | 1.584 | 0.880 | 0.792 | |
| Avg. SLGI[1]: | | | | 3.256 |
| | Elongation: 125% | F (g) | | |
| 1 | 160.25 | 126.83 | 121.08 | 17.143 |
| 2 | 144.60 | 107.86 | 102.40 | 14.904 |
| 3 | 132.05 | 105.59 | 100.14 | 14.187 |
| 4 | 137.08 | 118.77 | 113.66 | 15.519 |
| 5 | 144.72 | 116.60 | 112.21 | 15.688 |
| 6 | 142.86 | 116.68 | 112.98 | 15.646 |
| 7 | 156.36 | 125.53 | 121.40 | 16.938 |
| 8 | 154.97 | 113.89 | 110.42 | 15.930 |
| 9 | 133.83 | 106.00 | 101.22 | 14.324 |
| 10 | 147.34 | 112.54 | 106.60 | 15.392 |
| Avg. LGI[1]: | 6.107 | 4.831 | 4.629 | |
| Avg. SLGI[1]: | | | | 15.567 |
| | Elongation: 150% | F (g) | | |
| 1 | 247.48 | 204.31 | 197.11 | 27.254 |
| 2 | 239.52 | 191.86 | 184.81 | 25.880 |
| 3 | 226.26 | 189.34 | 182.34 | 25.113 |
| 4 | 229.06 | 200.22 | 193.75 | 26.167 |
| 5 | 235.14 | 199.58 | 193.60 | 26.389 |
| 6 | 232.89 | 197.77 | 192.68 | 26.180 |
| 7 | 246.76 | 205.25 | 200.16 | 27.391 |
| 8 | 239.74 | 193.85 | 190.02 | 26.192 |
| 9 | 226.85 | 190.28 | 184.08 | 25.251 |
| 10 | 237.18 | 192.14 | 185.80 | 25.835 |
| Avg. LGI[1]: | 9.916 | 8.251 | 7.998 | |
| Avg. SLGI[1]: | | | | 26.165 |
| | Elongation: 175% | F (g) | | |
| 1 | 323.63 | 275.39 | 265.86 | 36.325 |
| 2 | 316.10 | 267.34 | 257.79 | 35.332 |
| 3 | 302.59 | 259.82 | 250.24 | 34.131 |
| 4 | 308.96 | 271.10 | 262.13 | 35.372 |
| 5 | 310.85 | 268.91 | 262.11 | 35.359 |
| 6 | 309.31 | 266.99 | 260.19 | 35.133 |
| 7 | 325.68 | 277.08 | 270.40 | 36.673 |
| 8 | 311.02 | 262.69 | 257.74 | 34.921 |
| 9 | 298.83 | 256.82 | 249.61 | 33.821 |
| 10 | 308.20 | 261.44 | 253.19 | 34.559 |
| Avg. LGI[1]: | 13.084 | 11.204 | 10.875 | |
| Avg. SLGI[1]: | | | | 35.162 |

TABLE 1-continued

| | ULG 1 | Height (mm) | 42 | |
|---|---|---|---|---|
| Sample | Cycle 1 | Cycle 2 | Cycle 3 | SLGI |
| | Elongation: 195% | | F (g) | |
| 1 | 389.32 | 351.66 | 340.98 | 45.442 |
| 2 | 380.25 | 342.11 | 332.30 | 44.296 |
| 3 | 360.11 | 330.88 | 320.38 | 42.478 |
| 4 | 374.73 | 344.69 | 335.89 | 44.323 |
| 5 | 371.85 | 342.69 | 333.72 | 44.027 |
| 6 | 372.84 | 341.09 | 333.11 | 43.976 |
| 7 | 390.39 | 352.52 | 345.09 | 45.696 |
| 8 | 371.40 | 333.55 | 328.47 | 43.404 |
| 9 | 360.06 | 321.01 | 313.28 | 41.763 |
| 10 | 365.67 | 331.21 | 321.12 | 42.756 |
| Avg. LGI[1]: | 15.694 | 14.244 | 13.878 | |
| Avg. SLGI[1]: | | | | 43.816 |
| | | TOTALS: | | |
| | Avg. LGI[1]: | Cycle 1 | 9.277 | |
| | | Cycle 2 | 7.882 | |
| | | Cycle 3 | 7.634 | |
| | TLGI[1]: | 8.264 | | |

[1] units = kg*mm

TABLE 2

| | ULG 2 | Height (mm) | 42 | |
|---|---|---|---|---|
| Sample | Cycle 1 | Cycle 2 | Cycle 3 | SLGI |
| | Elongation: 105% | | F (g) | |
| 1 | 32.18 | 20.80 | 18.49 | 3.002 |
| 2 | 30.29 | 15.83 | 14.21 | 2.534 |
| 3 | 28.65 | 19.37 | 17.74 | 2.762 |
| 4 | 37.34 | 24.98 | 23.39 | 3.600 |
| 5 | 38.25 | 23.93 | 22.59 | 3.560 |
| 6 | 32.30 | 22.45 | 21.15 | 3.188 |
| 7 | 11.32 | 5.43 | 5.21 | 0.922 |
| 8 | 29.99 | 18.06 | 15.37 | 2.664 |
| 9 | 26.85 | 16.59 | 14.93 | 2.452 |
| 10 | 41.86 | 25.39 | 23.75 | 3.822 |
| Avg. LGI[1]: | 1.298 | 0.810 | 0.743 | |
| Avg. SLGI[1]: | | | | 2.850 |
| | Elongation: 125% | | F (g) | |
| 1 | 111.64 | 90.12 | 86.15 | 12.092 |
| 2 | 123.16 | 92.02 | 87.72 | 12.722 |
| 3 | 105.85 | 86.55 | 83.34 | 11.581 |
| 4 | 120.55 | 95.70 | 92.03 | 12.948 |
| 5 | 119.85 | 99.37 | 95.89 | 13.235 |
| 6 | 129.17 | 110.59 | 106.65 | 14.549 |
| 7 | 61.34 | 46.06 | 43.51 | 6.338 |
| 8 | 106.32 | 84.91 | 80.30 | 11.404 |
| 9 | 98.89 | 79.25 | 76.34 | 10.688 |
| 10 | 133.05 | 101.38 | 97.87 | 13.957 |
| Avg. LGI[1]: | 4.661 | 3.721 | 3.569 | |
| Avg. SLGI[1]: | | | | 11.951 |
| | Elongation: 150% | | F (g) | |
| 1 | 197.65 | 168.09 | 163.49 | 22.228 |
| 2 | 211.95 | 174.27 | 168.13 | 23.283 |
| 3 | 185.78 | 163.88 | 160.18 | 21.413 |
| 4 | 211.02 | 173.63 | 168.40 | 23.228 |
| 5 | 207.54 | 181.10 | 176.11 | 23.720 |
| 6 | 222.71 | 196.18 | 190.71 | 25.603 |
| 7 | 143.07 | 124.19 | 120.17 | 16.272 |
| 8 | 189.13 | 161.26 | 154.90 | 21.222 |
| 9 | 184.78 | 157.06 | 153.16 | 20.790 |
| 10 | 225.09 | 181.53 | 177.35 | 24.527 |
| Avg. LGI[1]: | 8.311 | 7.061 | 6.857 | |
| Avg. SLGI[1]: | | | | 22.229 |

TABLE 2-continued

| | ULG 2 | Height (mm) | 42 | |
|---|---|---|---|---|
| Sample | Cycle 1 | Cycle 2 | Cycle 3 | SLGI |
| | Elongation: 175% | | F (g) | |
| 1 | 280.95 | 242.74 | 235.98 | 31.906 |
| 2 | 286.55 | 246.04 | 238.54 | 32.387 |
| 3 | 252.17 | 230.22 | 225.31 | 29.723 |
| 4 | 294.94 | 251.44 | 244.07 | 33.199 |
| 5 | 289.66 | 257.95 | 250.92 | 33.538 |
| 6 | 302.24 | 269.37 | 262.14 | 35.018 |
| 7 | 211.47 | 195.61 | 190.34 | 25.092 |
| 8 | 271.29 | 238.03 | 229.75 | 31.041 |
| 9 | 259.70 | 229.28 | 224.19 | 29.953 |
| 10 | 305.49 | 257.95 | 251.95 | 34.246 |
| Avg. LGI[1]: | 11.569 | 10.158 | 9.883 | |
| Avg. SLGI[1]: | | | | 31.610 |
| | Elongation: 195% | | F (g) | |
| 1 | 349.30 | 314.94 | 308.52 | 40.856 |
| 2 | 346.33 | 315.67 | 307.00 | 40.698 |
| 3 | 308.39 | 291.46 | 286.01 | 37.206 |
| 4 | 363.46 | 330.72 | 321.84 | 42.673 |
| 5 | 358.91 | 335.52 | 327.33 | 42.914 |
| 6 | 368.09 | 343.97 | 335.84 | 44.012 |
| 7 | 264.38 | 251.89 | 245.73 | 32.004 |
| 8 | 335.26 | 309.09 | 301.30 | 39.717 |
| 9 | 315.71 | 293.68 | 288.07 | 37.693 |
| 10 | 371.30 | 334.61 | 327.37 | 43.398 |
| Avg. LGI[1]: | 14.201 | 13.111 | 12.806 | |
| Avg. SLGI[1]: | | | | 40.117 |
| | | TOTALS: | | |
| | Avg. LGI[1]: | Cycle 1 | 8.008 | |
| | | Cycle 2 | 6.972 | |
| | | Cycle 3 | 6.772 | |
| | TLGI[1]: | 7.251 | | |

[1] units = kg*mm

TABLE 3

| | ULG 3 | Height (mm) | 52 | |
|---|---|---|---|---|
| Sample | Cycle 1 | Cycle 2 | Cycle 3 | SLGI |
| | Elongation: 105% | | F (g) | |
| 1 | 25.70 | 13.47 | 11.03 | 2.610 |
| 2 | 19.48 | 10.64 | 9.45 | 2.058 |
| 3 | 12.96 | 4.64 | 4.42 | 1.145 |
| 4 | 17.01 | 7.50 | 7.35 | 1.657 |
| 5 | 16.98 | 7.01 | 6.29 | 1.575 |
| 6 | 23.18 | 11.51 | 10.73 | 2.362 |
| 7 | 17.97 | 7.56 | 7.21 | 1.702 |
| 8 | 14.98 | 7.06 | 6.10 | 1.463 |
| 9 | 22.79 | 12.03 | 11.45 | 2.406 |
| 10 | 21.59 | 12.28 | 11.21 | 2.344 |
| Avg. LGI[1]: | 1.002 | 0.487 | 0.443 | |
| Avg. SLGI[1]: | | | | 1.932 |
| | Elongation: 125% | | F (g) | |
| 1 | 69.08 | 54.51 | 50.88 | 9.072 |
| 2 | 65.56 | 49.39 | 46.80 | 8.411 |
| 3 | 50.75 | 35.14 | 33.24 | 6.195 |
| 4 | 62.37 | 45.97 | 44.18 | 7.931 |
| 5 | 58.57 | 44.56 | 42.42 | 7.569 |
| 6 | 67.54 | 49.24 | 47.56 | 8.546 |
| 7 | 64.44 | 46.60 | 44.95 | 8.111 |
| 8 | 55.83 | 41.35 | 38.85 | 7.074 |
| 9 | 68.42 | 52.47 | 50.28 | 8.901 |
| 10 | 69.34 | 51.38 | 48.67 | 8.808 |
| Avg. LGI[1]: | 3.286 | 2.447 | 2.329 | |
| Avg. SLGI[1]: | | | | 8.062 |

TABLE 3-continued

| | ULG 3 | Height (mm) | 52 | |
|---|---|---|---|---|
| Sample | Cycle 1 | Cycle 2 | Cycle 3 | SLGI |
| | | Elongation: 150% | F (g) | |
| 1 | 104.06 | 85.65 | 81.84 | 14.121 |
| 2 | 98.86 | 83.03 | 80.03 | 13.620 |
| 3 | 85.63 | 72.60 | 70.35 | 11.886 |
| 4 | 95.77 | 80.53 | 78.53 | 13.251 |
| 5 | 90.57 | 76.95 | 75.02 | 12.612 |
| 6 | 100.52 | 81.21 | 79.47 | 13.582 |
| 7 | 101.71 | 82.50 | 80.53 | 13.766 |
| 8 | 89.27 | 76.49 | 73.85 | 12.460 |
| 9 | 105.32 | 84.79 | 82.10 | 14.155 |
| 10 | 106.19 | 86.16 | 82.86 | 14.311 |
| Avg. LGI[1]: | 5.085 | 4.212 | 4.080 | |
| Avg. SLGI[1]: | | | | 13.376 |
| | | Elongation: 175% | F (g) | |
| 1 | 136.01 | 114.27 | 112.43 | 18.861 |
| 2 | 129.48 | 113.27 | 110.10 | 18.348 |
| 3 | 112.48 | 101.41 | 98.61 | 16.250 |
| 4 | 129.83 | 111.60 | 109.48 | 18.247 |
| 5 | 119.37 | 104.82 | 103.64 | 17.047 |
| 6 | 134.24 | 114.29 | 111.45 | 18.719 |
| 7 | 135.03 | 115.08 | 112.05 | 18.832 |
| 8 | 119.53 | 106.47 | 102.96 | 17.106 |
| 9 | 137.39 | 116.81 | 112.78 | 19.083 |
| 10 | 164.14 | 123.52 | 119.05 | 21.149 |
| Avg. LGI[1]: | 6.851 | 5.832 | 5.681 | |
| Avg. SLGI[1]: | | | | 18.364 |
| | | Elongation: 195% | F (g) | |
| 1 | 169.94 | 154.64 | 152.74 | 24.821 |
| 2 | 159.22 | 147.10 | 143.04 | 23.367 |
| 3 | 138.06 | 127.92 | 125.67 | 20.366 |
| 4 | 173.93 | 157.73 | 154.44 | 25.277 |
| 5 | 148.80 | 135.66 | 133.45 | 21.731 |
| 6 | 170.33 | 154.11 | 151.07 | 24.727 |
| 7 | 166.47 | 151.45 | 148.29 | 24.243 |
| 8 | 145.21 | 134.58 | 132.94 | 21.462 |
| 9 | 169.55 | 154.96 | 150.38 | 24.694 |
| 10 | 299.46 | 211.03 | 201.27 | 37.012 |
| Avg. LGI[1]: | 9.053 | 7.952 | 7.765 | |
| Avg. SLGI[1]: | | | | 24.770 |
| | TOTALS: | | | |
| | Avg. LGI[1]: | Cycle 1 | 5.055 | |
| | | Cycle 2 | 4.186 | |
| | | Cycle 3 | 4.060 | |
| | TLGI[1]: | | 4.434 | |

[1]units = kg*mm

TABLE 4

| | ULG 4 | Height (mm) | 28 | |
|---|---|---|---|---|
| Sample | Cycle 1 | Cycle 2 | Cycle 3 | SLGI |
| | | Elongation: 105% | F (g) | |
| 1 | 19.53 | 11.98 | 11.75 | 1.211 |
| 2 | 15.94 | 7.31 | 6.77 | 0.841 |
| 3 | 14.40 | 6.35 | 5.60 | 0.738 |
| 4 | 26.20 | 14.30 | 12.57 | 1.486 |
| 5 | 16.55 | 10.88 | 10.17 | 1.053 |
| 6 | 18.79 | 8.87 | 7.42 | 0.982 |
| 7 | 19.92 | 10.05 | 8.16 | 1.068 |
| 8 | 22.53 | 12.91 | 11.66 | 1.319 |
| 9 | 13.22 | 7.79 | 6.51 | 0.771 |
| 10 | 22.13 | 11.31 | 11.16 | 1.249 |
| Avg. LGI[1]: | 0.530 | 0.285 | 0.257 | |
| Avg. SLGI[1]: | | | | 1.072 |
| | | Elongation: 125% | F (g) | |
| 1 | 61.37 | 49.19 | 47.60 | 4.428 |
| 2 | 52.44 | 41.43 | 40.18 | 3.753 |
| 3 | 46.48 | 35.21 | 33.55 | 3.227 |
| 4 | 82.29 | 58.00 | 55.12 | 5.471 |
| 5 | 61.00 | 48.52 | 47.01 | 4.383 |
| 6 | 59.28 | 44.02 | 41.77 | 4.062 |
| 7 | 64.81 | 51.06 | 48.03 | 4.589 |
| 8 | 64.43 | 49.24 | 46.63 | 4.488 |
| 9 | 49.22 | 38.15 | 36.11 | 3.457 |
| 10 | 68.63 | 50.26 | 49.07 | 4.703 |
| Avg. LGI[1]: | 1.708 | 1.302 | 1.246 | |
| Avg. SLGI[1]: | | | | 4.256 |
| | | Elongation: 150% | F (g) | |
| 1 | 110.73 | 92.92 | 90.53 | 8.237 |
| 2 | 97.61 | 80.52 | 78.62 | 7.189 |
| 3 | 88.21 | 72.91 | 70.71 | 6.491 |
| 4 | 151.75 | 106.87 | 102.54 | 10.112 |
| 5 | 114.26 | 93.53 | 90.95 | 8.365 |
| 6 | 108.40 | 87.52 | 85.65 | 7.884 |
| 7 | 114.69 | 96.12 | 92.08 | 8.481 |
| 8 | 118.88 | 93.53 | 90.61 | 8.485 |
| 9 | 89.81 | 76.24 | 73.58 | 6.710 |
| 10 | 121.21 | 94.93 | 92.71 | 8.648 |
| Avg. LGI[1]: | 3.124 | 2.506 | 2.430 | |
| Avg. SLGI[1]: | | | | 8.060 |
| | | Elongation: 175% | F (g) | |
| 1 | 170.77 | 145.62 | 141.81 | 12.830 |
| 2 | 150.63 | 127.20 | 123.45 | 11.236 |
| 3 | 139.34 | 119.17 | 115.60 | 10.475 |
| 4 | 239.33 | 172.31 | 164.34 | 16.127 |
| 5 | 178.88 | 146.70 | 141.51 | 13.079 |
| 6 | 169.52 | 141.24 | 136.49 | 12.523 |
| 7 | 176.72 | 144.55 | 140.18 | 12.921 |
| 8 | 188.15 | 149.92 | 144.36 | 13.508 |
| 9 | 145.06 | 123.03 | 119.79 | 10.861 |
| 10 | 186.38 | 148.06 | 144.21 | 13.402 |
| Avg. LGI[1]: | 4.885 | 3.970 | 3.841 | |
| Avg. SLGI[1]: | | | | 12.696 |
| | | Elongation: 195% | F (g) | |
| 1 | 232.80 | 207.03 | 201.58 | 17.959 |
| 2 | 198.79 | 177.94 | 173.08 | 15.395 |
| 3 | 190.03 | 170.64 | 165.31 | 14.727 |
| 4 | 359.60 | 289.46 | 274.72 | 25.866 |
| 5 | 246.61 | 217.71 | 209.91 | 18.878 |
| 6 | 224.26 | 200.46 | 194.77 | 17.346 |
| 7 | 241.99 | 212.21 | 204.86 | 18.454 |
| 8 | 260.54 | 226.45 | 218.36 | 19.750 |
| 9 | 200.76 | 179.77 | 175.16 | 15.559 |
| 10 | 249.38 | 215.64 | 210.24 | 18.907 |
| Avg. LGI[1]: | 6.733 | 5.872 | 5.678 | |
| Avg. SLGI[1]: | | | | 18.284 |
| | TOTALS: | | | |
| | Avg. LGI[1]: | Cycle 1 | 3.396 | |
| | | Cycle 2 | 2.787 | |
| | | Cycle 3 | 2.691 | |
| | TLGI[1]: | | 2.958 | |

[1]units = kg*mm

TABLE 5

| | ULG 5 | Height (mm) | 28 | |
|---|---|---|---|---|
| Sample | Cycle 1 | Cycle 2 | Cycle 3 | SLGI |
| | Elongation: 105% | | F (g) | |
| 1 | 18.48 | 10.33 | 9.88 | 1.083 |
| 2 | 16.95 | 7.07 | 6.75 | 0.862 |
| 3 | 20.18 | 11.05 | 10.06 | 1.156 |
| 4 | 16.26 | 9.51 | 8.89 | 0.970 |
| 5 | 16.50 | 9.74 | 8.85 | 0.983 |
| 6 | 19.91 | 8.25 | 7.64 | 1.002 |
| 7 | 15.98 | 7.24 | 7.22 | 0.852 |
| 8 | 16.69 | 7.21 | 6.06 | 0.839 |
| 9 | 20.84 | 11.62 | 10.99 | 1.217 |
| 10 | 23.22 | 11.34 | 9.69 | 1.239 |
| Avg. LGI[1]: | 0.518 | 0.261 | 0.241 | |
| Avg. SLGI[1]: | | | | 1.020 |
| | Elongation: 125% | | F (g) | |
| 1 | 58.38 | 50.22 | 49.10 | 4.416 |
| 2 | 55.55 | 44.72 | 43.61 | 4.029 |
| 3 | 63.31 | 53.90 | 52.21 | 4.744 |
| 4 | 61.26 | 52.53 | 51.45 | 4.627 |
| 5 | 53.18 | 44.82 | 43.32 | 3.957 |
| 6 | 62.23 | 49.34 | 48.45 | 4.481 |
| 7 | 51.63 | 41.91 | 41.06 | 3.769 |
| 8 | 58.90 | 48.10 | 46.68 | 4.303 |
| 9 | 62.71 | 52.08 | 51.18 | 4.647 |
| 10 | 67.48 | 55.17 | 53.18 | 4.923 |
| Avg. LGI[1]: | 1.665 | 1.380 | 1.345 | |
| Avg. SLGI[1]: | | | | 4.389 |
| | Elongation: 150% | | F (g) | |
| 1 | 95.91 | 88.77 | 87.93 | 7.633 |
| 2 | 95.35 | 84.92 | 83.25 | 7.379 |
| 3 | 107.52 | 97.93 | 95.53 | 8.427 |
| 4 | 101.85 | 92.52 | 90.98 | 7.990 |
| 5 | 92.00 | 81.33 | 79.92 | 7.091 |
| 6 | 101.92 | 89.80 | 88.20 | 7.838 |
| 7 | 89.20 | 80.30 | 79.02 | 6.959 |
| 8 | 96.40 | 87.40 | 85.73 | 7.547 |
| 9 | 102.22 | 89.63 | 88.09 | 7.838 |
| 10 | 105.36 | 94.28 | 91.89 | 8.163 |
| Avg. LGI[1]: | 2.766 | 2.483 | 2.438 | |
| Avg. SLGI[1]: | | | | 7.686 |
| | Elongation: 175% | | F (g) | |
| 1 | 130.06 | 123.65 | 122.13 | 10.524 |
| 2 | 133.09 | 121.50 | 119.06 | 10.462 |
| 3 | 158.23 | 142.56 | 138.97 | 12.313 |
| 4 | 140.22 | 129.18 | 126.92 | 11.097 |
| 5 | 124.52 | 114.24 | 112.34 | 9.831 |
| 6 | 141.12 | 127.70 | 125.11 | 11.030 |
| 7 | 123.48 | 114.03 | 112.34 | 9.796 |
| 8 | 128.59 | 121.10 | 118.90 | 10.321 |
| 9 | 137.01 | 123.60 | 121.59 | 10.702 |
| 10 | 140.17 | 129.43 | 126.86 | 11.101 |
| Avg. LGI[1]: | 3.798 | 3.492 | 3.428 | |
| Avg. SLGI[1]: | | | | 10.718 |
| | Elongation: 195% | | F (g) | |
| 1 | 163.04 | 158.28 | 156.37 | 13.375 |
| 2 | 169.71 | 159.93 | 156.93 | 13.624 |
| 3 | 220.36 | 203.10 | 198.96 | 17.428 |
| 4 | 182.41 | 171.88 | 169.21 | 14.658 |
| 5 | 153.48 | 144.63 | 142.27 | 12.331 |
| 6 | 185.06 | 172.70 | 169.06 | 14.751 |
| 7 | 153.99 | 147.13 | 144.84 | 12.487 |
| 8 | 159.87 | 153.11 | 151.38 | 13.002 |
| 9 | 168.60 | 158.53 | 155.78 | 13.521 |
| 10 | 175.31 | 165.49 | 163.80 | 14.129 |
| Avg. LGI[1]: | 4.849 | 4.577 | 4.504 | |
| Avg. SLGI[1]: | | | | 13.931 |
| | TOTALS: | | | |
| Avg. LGI[1]: | | Cycle 1 | 2.719 | |
| | | Cycle 2 | 2.439 | |
| | | Cycle 3 | 2.391 | |
| TLGI[1]: | 2.516 | | | |

[1]units = kg*mm

TABLE 6

| | ULG 6 | Height (mm) | 28 | |
|---|---|---|---|---|
| Sample | Cycle 1 | Cycle 2 | Cycle 3 | SLGI |
| | Elongation: 105% | | F (g) | |
| 1 | 15.21 | 6.60 | 5.59 | 0.767 |
| 2 | 13.93 | 9.53 | 9.07 | 0.911 |
| 3 | 10.97 | 7.53 | 7.03 | 0.715 |
| 4 | 15.18 | 8.02 | 7.63 | 0.863 |
| 5 | 13.58 | 6.32 | 5.98 | 0.725 |
| 6 | 12.74 | 7.08 | 6.44 | 0.735 |
| 7 | 12.56 | 8.26 | 7.67 | 0.798 |
| 8 | 15.45 | 6.05 | 5.48 | 0.755 |
| 9 | 14.94 | 9.02 | 7.61 | 0.884 |
| 10 | 13.52 | 9.00 | 8.72 | 0.875 |
| Avg. LGI[1]: | 0.387 | 0.217 | 0.199 | |
| Avg. SLGI[1]: | | | | 0.803 |
| | Elongation: 125% | | F (g) | |
| 1 | 40.50 | 30.64 | 29.58 | 2.820 |
| 2 | 43.82 | 35.83 | 35.13 | 3.214 |
| 3 | 35.89 | 30.28 | 29.79 | 2.687 |
| 4 | 43.32 | 34.32 | 33.25 | 3.105 |
| 5 | 39.11 | 29.60 | 28.67 | 2.727 |
| 6 | 40.21 | 32.71 | 31.74 | 2.930 |
| 7 | 37.23 | 32.58 | 31.45 | 2.835 |
| 8 | 43.81 | 33.53 | 32.58 | 3.078 |
| 9 | 40.43 | 33.35 | 31.39 | 2.945 |
| 10 | 39.71 | 32.76 | 31.93 | 2.923 |
| Avg. LGI[1]: | 1.131 | 0.912 | 0.883 | |
| Avg. SLGI[1]: | | | | 2.926 |
| | Elongation: 150% | | F (g) | |
| 1 | 68.13 | 57.37 | 55.59 | 5.071 |
| 2 | 75.42 | 62.05 | 60.65 | 5.547 |
| 3 | 64.65 | 55.72 | 54.29 | 4.890 |
| 4 | 74.48 | 60.79 | 59.24 | 5.446 |
| 5 | 64.26 | 54.38 | 53.53 | 4.821 |
| 6 | 72.75 | 59.68 | 58.39 | 5.343 |
| 7 | 64.51 | 56.67 | 55.78 | 4.955 |
| 8 | 75.66 | 59.19 | 57.93 | 5.398 |
| 9 | 68.82 | 57.84 | 55.92 | 5.112 |
| 10 | 69.06 | 57.50 | 56.66 | 5.130 |
| Avg. LGI[1]: | 1.954 | 1.627 | 1.590 | |
| Avg. SLGI[1]: | | | | 5.171 |
| | Elongation: 175% | | F (g) | |
| 1 | 100.85 | 86.27 | 83.93 | 7.589 |
| 2 | 110.86 | 91.94 | 89.87 | 8.195 |
| 3 | 95.58 | 82.55 | 80.60 | 7.244 |
| 4 | 108.28 | 91.40 | 88.82 | 8.078 |
| 5 | 92.01 | 80.23 | 78.76 | 7.028 |
| 6 | 113.59 | 93.52 | 90.57 | 8.335 |
| 7 | 97.27 | 84.17 | 82.08 | 7.379 |
| 8 | 112.68 | 91.55 | 88.84 | 8.206 |
| 9 | 94.61 | 83.13 | 80.37 | 7.227 |
| 10 | 100.95 | 85.10 | 83.05 | 7.535 |
| Avg. LGI[1]: | 2.875 | 2.436 | 2.371 | |
| Avg. SLGI[1]: | | | | 7.682 |

TABLE 6-continued

| | ULG 6 | Height (mm) | 28 | |
|---|---|---|---|---|
| Sample | Cycle 1 | Cycle 2 | Cycle 3 | SLGI |
| | Elongation: 195% | F (g) | | |
| 1 | 137.45 | 122.47 | 120.89 | 10.663 |
| 2 | 147.56 | 130.70 | 126.65 | 11.337 |
| 3 | 126.34 | 115.12 | 112.20 | 9.902 |
| 4 | 145.07 | 131.51 | 127.33 | 11.309 |
| 5 | 120.33 | 110.72 | 108.25 | 9.500 |
| 6 | 158.93 | 141.60 | 136.98 | 12.250 |
| 7 | 128.81 | 116.70 | 113.74 | 10.059 |
| 8 | 154.09 | 137.90 | 134.26 | 11.935 |
| 9 | 120.45 | 110.33 | 108.40 | 9.497 |
| 10 | 129.06 | 117.74 | 115.23 | 10.137 |
| Avg. LGI[1]: | 3.831 | 3.457 | 3.371 | |
| Avg. SLGI[1]: | | | | 10.659 |
| | TOTALS: | | | |
| Avg. LGI[1]: | Cycle 1 | 2.035 | | |
| | Cycle 2 | 1.730 | | |
| | Cycle 3 | 1.683 | | |
| TLGI[1]: | 1.816 | | | |

[1]units = kg*mm

TABLE 7

| | ULG 7 | Height (mm) | 28 | |
|---|---|---|---|---|
| Sample | Cycle 1 | Cycle 2 | Cycle 3 | SLGI |
| | Elongation: 105% | F (g) | | |
| 1 | 13.77 | 7.93 | 7.33 | 0.813 |
| 2 | 11.78 | 6.33 | 5.34 | 0.657 |
| 3 | 14.16 | 7.10 | 6.88 | 0.788 |
| 4 | 15.35 | 7.95 | 7.74 | 0.869 |
| 5 | 16.64 | 8.08 | 7.94 | 0.914 |
| 6 | 14.64 | 6.00 | 5.23 | 0.724 |
| 7 | 13.80 | 7.67 | 7.23 | 0.804 |
| 8 | 13.04 | 6.88 | 5.63 | 0.715 |
| 9 | 13.22 | 8.39 | 8.18 | 0.834 |
| 10 | 15.66 | 8.84 | 7.21 | 0.888 |
| Avg. LGI[1]: | 0.398 | 0.210 | 0.192 | |
| Avg. SLGI[1]: | | | | 0.801 |
| | Elongation: 125% | F (g) | | |
| 1 | 35.38 | 30.98 | 29.94 | 2.696 |
| 2 | 38.29 | 31.47 | 30.31 | 2.802 |
| 3 | 36.23 | 29.97 | 29.48 | 2.679 |
| 4 | 39.84 | 31.92 | 31.58 | 2.894 |
| 5 | 39.52 | 31.43 | 30.82 | 2.850 |
| 6 | 36.29 | 28.58 | 27.70 | 2.592 |
| 7 | 38.66 | 32.24 | 31.84 | 2.877 |
| 8 | 35.53 | 30.12 | 28.86 | 2.646 |
| 9 | 36.66 | 30.76 | 30.47 | 2.741 |
| 10 | 38.72 | 30.49 | 28.93 | 2.748 |
| Avg. LGI[1]: | 1.050 | 0.862 | 0.840 | |
| Avg. SLGI[1]: | | | | 2.752 |
| | Elongation: 150% | F (g) | | |
| 1 | 56.92 | 49.83 | 49.84 | 4.385 |
| 2 | 64.25 | 56.10 | 54.35 | 4.892 |
| 3 | 60.35 | 51.79 | 51.44 | 4.580 |
| 4 | 61.15 | 54.45 | 53.53 | 4.736 |
| 5 | 61.28 | 53.65 | 53.02 | 4.703 |
| 6 | 56.49 | 49.46 | 48.63 | 4.328 |
| 7 | 65.92 | 55.39 | 54.66 | 4.927 |
| 8 | 56.71 | 52.44 | 50.93 | 4.482 |

TABLE 7-continued

| | ULG 7 | Height (mm) | 28 | |
|---|---|---|---|---|
| Sample | Cycle 1 | Cycle 2 | Cycle 3 | SLGI |
| 9 | 61.55 | 53.50 | 53.10 | 4.708 |
| 10 | 60.16 | 52.91 | 50.90 | 4.591 |
| Avg. LGI[1]: | 1.693 | 1.483 | 1.457 | |
| Avg. SLGI[1]: | | | | 4.633 |
| | Elongation: 175% | F (g) | | |
| 1 | 80.40 | 71.08 | 70.54 | 6.217 |
| 2 | 94.03 | 80.91 | 80.18 | 7.143 |
| 3 | 81.57 | 73.28 | 72.27 | 6.359 |
| 4 | 86.76 | 77.37 | 75.98 | 6.723 |
| 5 | 84.52 | 75.89 | 74.46 | 6.576 |
| 6 | 77.51 | 69.68 | 68.29 | 6.033 |
| 7 | 94.11 | 80.46 | 79.15 | 7.104 |
| 8 | 78.93 | 72.82 | 71.93 | 6.263 |
| 9 | 83.78 | 76.83 | 75.52 | 6.612 |
| 10 | 83.70 | 75.22 | 73.18 | 6.499 |
| Avg. LGI[1]: | 2.367 | 2.110 | 2.076 | |
| Avg. SLGI[1]: | | | | 6.553 |
| | Elongation: 195% | F (g) | | |
| 1 | 102.78 | 94.84 | 94.18 | 8.170 |
| 2 | 133.64 | 121.98 | 119.70 | 10.509 |
| 3 | 103.34 | 96.88 | 95.34 | 8.276 |
| 4 | 110.48 | 103.61 | 101.86 | 8.847 |
| 5 | 106.78 | 99.41 | 98.65 | 8.536 |
| 6 | 95.65 | 90.14 | 88.81 | 7.689 |
| 7 | 119.66 | 109.78 | 107.94 | 9.447 |
| 8 | 100.19 | 94.13 | 92.83 | 8.040 |
| 9 | 107.80 | 102.27 | 100.54 | 8.697 |
| 10 | 105.54 | 97.92 | 97.03 | 8.414 |
| Avg. LGI[1]: | 3.040 | 2.831 | 2.791 | |
| Avg. SLGI[1]: | | | | 8.662 |
| | TOTALS: | | | |
| Avg. LGI[1]: | Cycle 1 | 1.710 | | |
| | Cycle 2 | 1.499 | | |
| | Cycle 3 | 1.471 | | |
| TLGI[1]: | 1.560 | | | |

[1]units = kg*mm

TABLE 8

Mean LGI, TLGI and SLGI Values for LGs 1–7 For Cycles 1–3

| 105% Elongation | | Avg. F[1] | LGI[3] | SLGI | |
|---|---|---|---|---|---|
| LG | H (mm) | (gm) | (kg*mm) | (kg*mm) | %[2] |
| 1 | 42 | 25.844 | 1.085 | 3.256 | 68.5% |
| 2 | 42 | 22.623 | 0.950 | 2.850 | 47.5% |
| 3 | 52 | 12.386 | 0.644 | 1.932 | — |
| 4 | 28 | 12.758 | 0.357 | 1.072 | −44.5% |
| 5 | 28 | 12.147 | 0.340 | 1.020 | −47.2% |
| 6 | 28 | 9.557 | 0.268 | 0.803 | −58.5% |
| 7 | 28 | 9.531 | 0.267 | 0.801 | −58.6% |

| 125% Elongation | | Avg. F[1] | LGI[3] | SLGI | |
|---|---|---|---|---|---|
| LG | H (mm) | (gm) | (kg*mm) | (kg*mm) | %[2] |
| 1 | 42 | 123.549 | 5.189 | 15.567 | 93.1% |
| 2 | 42 | 94.852 | 3.984 | 11.951 | 48.2% |
| 3 | 52 | 51.678 | 2.687 | 8.062 | — |
| 4 | 28 | 50.670 | 1.419 | 4.256 | −47.2% |
| 5 | 28 | 52.255 | 1.463 | 4.389 | −45.6% |
| 6 | 28 | 34.838 | 0.975 | 2.926 | −63.7% |
| 7 | 28 | 32.767 | 0.917 | 2.752 | −65.9% |

TABLE 8-continued

| 150% Elongation | | Avg. F[1] | LGI[3] | SLGI | |
|---|---|---|---|---|---|
| LG | H (mm) | (gm) | (kg*mm) | (kg*mm) | %[2] |
| 1 | 42 | 207.661 | 8.722 | 26.165 | 95.6% |
| 2 | 42 | 176.417 | 7.410 | 22.229 | 66.2% |
| 3 | 52 | 85.746 | 4.459 | 13.376 | — |
| 4 | 28 | 95.954 | 2.687 | 8.060 | −39.7% |
| 5 | 28 | 91.505 | 2.562 | 7.686 | −42.5% |
| 6 | 28 | 61.564 | 1.724 | 5.171 | −61.3% |
| 7 | 28 | 55.157 | 1.544 | 4.633 | −65.4% |

| 175% Elongation | | Avg. F[1] | LGI[3] | SLGI | |
|---|---|---|---|---|---|
| LG | H (mm) | (gm) | (kg*mm) | (kg*mm) | %[2] |
| 1 | 42 | 279.067 | 11.721 | 35.162 | 91.5% |
| 2 | 42 | 250.876 | 10.537 | 31.610 | 72.1% |
| 3 | 52 | 117.720 | 6.121 | 18.364 | — |
| 4 | 28 | 151.144 | 4.232 | 12.696 | −30.9% |
| 5 | 28 | 127.590 | 3.573 | 10.718 | −41.6% |
| 6 | 28 | 91.448 | 2.561 | 7.682 | −58.2% |
| 7 | 28 | 78.012 | 2.184 | 6.553 | −64.3% |

| 195% Elongation | | Avg. F[1] | LGI[3] | SLGI | |
|---|---|---|---|---|---|
| LG | H (mm) | (gm) | (kg*mm) | (kg*mm) | %[2] |
| 1 | 42 | 347.746 | 14.605 | 43.816 | 76.9% |
| 2 | 42 | 318.390 | 13.372 | 40.117 | 62.0% |
| 3 | 52 | 158.781 | 8.257 | 24.770 | — |
| 4 | 28 | 217.669 | 6.095 | 18.284 | −26.2% |
| 5 | 28 | 165.840 | 4.644 | 13.931 | −43.8% |
| 6 | 28 | 126.894 | 3.553 | 10.659 | −57.0% |
| 7 | 28 | 103.123 | 2.887 | 8.662 | −65.0% |

| TLGI/Average SLGI | | | | |
|---|---|---|---|---|
| LG | H (mm) | TLGI (kg*mm) | Avg. SLGI (kg*mm) | %[2] |
| 1 | 42 | 8.264 | 24.793 | 86.4% |
| 2 | 42 | 7.251 | 21.752 | 63.5% |
| 3 | 52 | 4.434 | 13.301 | — |
| 4 | 28 | 2.958 | 8.874 | −33.3% |
| 5 | 28 | 2.516 | 7.549 | −43.2% |
| 6 | 28 | 1.816 | 5.448 | −59.0% |
| 7 | 28 | 1.560 | 4.680 | −64.8% |

[1]elastic contractile force (measured in grams)
[2]percent difference between respective LG and the best known LG
[3]mean LGI over 3 cycles

TABLE 9

Mean ALGI Values for LGs 1–7 For Cycles 1–3

| LG | Cycle 1 | Cycle 2 | Cycle 3 | Avg. | %[3] |
|---|---|---|---|---|---|
| | Total ALGI[1] (kg*mm) | | | | |
| 1 | 46.385 | 45.680 | 38.172 | 43.412 | 85.2% |
| 2 | 40.039 | 39.551 | 33.858 | 37.816 | 61.3% |
| 3 | 25.277 | 24.762 | 20.298 | 23.446 | — |
| 4 | 16.980 | 16.735 | 13.453 | 15.723 | −32.9% |
| 5 | 13.596 | 13.339 | 11.955 | 12.963 | −44.7% |
| 6 | 10.177 | 10.007 | 8.415 | 9.533 | −59.3% |
| 7 | 8.549 | 8.361 | 7.357 | 8.089 | −65.5% |
| | Partial ALGI[2] (kg*mm) (150%-175%-195%) | | | | |
| 1 | 38.693 | 33.699 | 32.751 | 35.048 | 86.1% |
| 2 | 34.080 | 30.330 | 29.546 | 31.319 | 66.3% |
| 3 | 20.989 | 17.995 | 17.526 | 18.837 | — |
| 4 | 14.742 | 12.349 | 11.950 | 13.013 | −30.9% |
| 5 | 11.413 | 10.552 | 10.369 | 10.778 | −42.8% |

TABLE 9-continued

Mean ALGI Values for LGs 1–7 For Cycles 1–3

| LG | Cycle 1 | Cycle 2 | Cycle 3 | Avg. | %[3] |
|---|---|---|---|---|---|
| 6 | 8.659 | 7.520 | 7.333 | 7.837 | −58.4% |
| 7 | 7.101 | 6.423 | 6.325 | 6.616 | −64.9% |

[1]ALGI for 105%, 125%, 150%, 175% and 195% elongations
[2]ALGI for 150%, 175%, and 195% elongations
[3]percent difference between respective LG and the best known LG

TABLE 10

TLGI Comparison

| LG | TLGI[1] (kg*mm) | %[2] |
|---|---|---|
| 1 | 8.264 | 86.4% |
| 2 | 7.251 | 63.5% |
| 3 | 4.434 | — |
| 4 | 2.958 | −33.3% |
| 5 | 2.516 | −43.2% |
| 6 | 1.816 | −59.0% |
| 7 | 1.560 | −64.8% |

[1]TLGI for 105%, 125% 150%, 175%, and 195% elongations over 3 cycles
[2]percent difference between respective LG and the best known LG As revealed by Table 8, the embodiments of the present invention (LG 1 and LG 2) disclosed herein exhibit, without exception, mean LGI, SLGI, and TLGI values substantially higher than the highest mean LGI, SLGI, and TLGI values of presently available standing leg gathers. For example, at an elongation 175%, LG 1 and LG 2 exhibit mean LGI values that are 91.5% and 72.1%, respectively, higher than the highest mean LGI value of a commercially available standing leg gather (LG 3) for the same elongation. Likewise, the mean total LGI and SLGI values for the LG 1 and LG 2 (embodiments of the present invention) are 86.4% and 63.5% higher than the highest average LGI and SLGI values for the commercially available standing leg gathers (LGs 3–7), where the term "mean total" is used herein to represent the statistical average, i.e. mean, of all of the measured LGI/SLGI values over the five specified elongation lengths (105%, 125%, 150%, 175%, and 195%).

The inventors have found that the leak containment ability of a standing leg gather is directly proportional to the LGI of the standing leg gather. This is shown, for example, in FIGS. 8 and 9 (where Garment 1 is LG-4, and Garment 2 is LG-1), which show that the present invention has an average leak containment ability at least 63.5%, and in some cases at least 86.4%, higher than conventional standing leg gathers, all else being equal. Indeed, the only leak containment difference between Garment 1 (LG-4) and Garment 2 (LG-1) in FIGS. 8 and 9 is the standing leg gathers (the other difference, which would not contribute to leakage, is the manner in which the elastic material is bonded to the non-woven sheet).

As shown in the above tables, the standing leg gathers in accordance with the present invention have a mean TLGI over three elongation cycles of at least about 4.75 kg*mm, preferably at least about 5.5 kg*mm, more preferably at least about 7 kg*mm, and most preferably at least about 8 kg*mm. Likewise, embodiments of the present invention have a mean SLGI at 150% elongation for three elongation cycles of at least about 15 kg*mm, preferably at least about 18 kg*mm, more preferably at least about 21 kg*mm, and most preferably about 25 kg*mm. Similarly, standing leg gathers in accordance with the present invention have a mean SLGI at 175% elongation for three elongation cycles of at least about 20 kg*mm, preferably at least about 25 kg*mm, more preferably at least about 30 kg*mm, and most preferably at least about 35 kg*mm. At an elongation of 195%, embodiments of the present invention have a mean SLGI for three elongation cycles of at least about 25 kg*mm, preferably at least about 30 kg*mm, more preferably at least about 35 kg*mm, and most preferably at least about 40 kg*mm.

It will be appreciated that the difference between the various mean Leg Gasketing Indices of the present inventions and those of the commercially available standing leg gathers are statistically significant (between 62.0% and 86.1% different). Since it has been found that the LGI value for a standing leg gather is related to the ability of the standing leg gather to "gasket" against the wearer's body, and since the "gasketing" ability of a standing leg gather is related to the ability of the standing leg gather to minimize leakage (everything else being equal), it follows that the higher the LGI (and/or ALGI, SLGI, TLGI) value for a standing leg gather, the greater the ability of the standing leg gather to prevent leaks, everything else being equal.

The illustrated embodiments of the present invention demonstrate significantly higher LGI values compared to the presently available standing leg gathers. It therefore follows that present invention exhibits a significantly greater leak containment ability compared to these presently available standing leg gathers. As shown in the Tables above, the present invention encompasses standing leg gathers having a mean LGI at an elongation of about 150% for a first cycle of at least about 5.5 kg*mm, preferably at least about 6.75 kg*mm, more preferably at least about 8 kg*mm, and most preferably at least about 9 kg*mm. For a second cycle at an elongation length of 150%, the present invention includes standing leg gathers having a mean LGI of at least about 4.75 kg*mm, preferably at least about 6 kg*mm, more preferably at least about 7 kg*mm, and most preferably at least about 8 kg*mm. For a third cycle of an elongation length of 150%, the present invention includes standing leg gathers having a mean LGI of at least about 4.5 kg*mm, preferably at least about 5.5 kg*mm, more preferably at least about 6.5 kg*mm, and most preferably at least about 7.75 kg*mm.

At an elongation of 175%, the present invention includes standing leg gathers having a mean first cycle LGI of at least about 7.25 kg*mm, preferably at least about 9 kg*mm, more preferably at least about 11 kg*mm, and most preferably at least about 13 kg*mm. Likewise, embodiments of the present invention have a mean second LGI at 175% elongation of at least about 6.25 kg*mm, preferably at least about 8 kg*mm, more preferably at least about 10 kg*mm, and most preferably at least about 11 kg*mm. For a third cycle at 175% elongation, the present invention includes standing leg gathers having a mean LGI of at least about 6 kg*mm, preferably at least about 7.5 kg*mm, more preferably at least about 9 kg*mm, and most preferably at least about 10.5 kg*mm.

At an elongation of 195%, standing leg gathers in accordance with the present invention have a mean first cycle LGI of at least about 9.25 kg*mm, preferably at least about 11 kg*mm, more preferably at least about 13 kg*mm, and most preferably at least about 14 kg*mm. For a second cycle at an elongation of 195%, embodiments of the present invention have a mean LGI of at least about 8.25 kg*mm, preferably at least about 10 kg*mm, more preferably at least about 12 kg*mm, and most preferably at least about 13 kg*mm. The present invention includes standing leg gathers having a mean third cycle LGI at 195% elongation of at least about 8 kg*mm, preferably at least about 10 kg*mm, more preferably at least about 11 kg*mm, and most preferably at least about 12.5 kg*mm.

Table 9 illustrates the mean ALGI values for LGs 1–7 as computed for three cycles and force measurements taken at 105%, 125%, 150%, 175%, and 195% elongations. The mean ALGI for all five of these elongation lengths is referred to herein as the "mean total ALGI", whereas the mean ALGI for the latter three elongation lengths (i.e., 150%, 175% and 195% elongation) is herein referred to as the "mean partial ALGI". The mean partial ALGI is more likely to demonstrate the leak containment ability of a standing leg gather since, when worn on a wearer, a standing leg gather typically is elongated, or "stretched", to a length of between 140% and 200% of the unloaded length of the standing leg gather.

As Table 9 illustrates, the preferred embodiments of the present invention exhibit mean total ALGI values at least 61.3% higher the mean total ALGI values of the commercially available standing leg gathers, and values at least 66.3% higher when the mean partial ALGI values of the present invention when compared to the presently known standing leg gathers. Since the ALGI can be viewed as an indicator of the leak containment ability of a standing leg gather over a range of elongation lengths, it will be understood that the standing leg gathers in accordance with the present invention (LG 1 and LG 2) demonstrate significant improvement in the average leak containment ability over a range of elongations, the range preferably including elongations between 150% and 195% of the unloaded length, and more preferably between the unloaded length and a maximum elongation length determined by the material and structure of the standing leg gather.

With regards to three cycles of elongations of 105%, 125%, 150%, 175% and 195%, embodiments of the present invention have a mean total ALGI for a first cycle of at least about 27 kg*mm, preferably at least about 31 kg*mm, more preferably at least about 35 kg*mm, more preferably at least about 40 kg*mm, and most preferably at least about 45 kg*mm. For a second cycle, embodiments of the present invention have a mean total ALGI of at least about 27 kg*mm, preferably at least about 30 kg*mm, more preferably at least about 35 kg*mm, more preferably at least about 39 kg*mm, and most preferably at least about 44 kg*mm. Those standing leg gathers in accordance with the present invention have a third cycle mean total ALGI of at least about 22, preferably at least about 25 kg*mm, more preferably at least about 29 kg*mm, more preferably at least about 33 kg*mm, and most preferably at least about 37 kg*mm.

Likewise, those embodiments in accordance with the present invention have a mean first cycle partial ALGI for 150%, 175% and 195% elongation of at least about 23 kg*mm, preferably at least about 24 kg*mm, more preferably at least about 28 kg*mm, more preferably at least about 30 kg*mm, and most preferably at least about 34 kg*mm. Embodiments of the present invention have a mean second cycle partial ALGI for 150% 175% and 195% elongation of at least about 19 kg*mm, preferably at least about 22 kg*mm, more preferably at least about 25 kg*mm, more preferably at least about 28 kg*mm, and most preferably at least about 30 kg*mm. For a third cycle, embodiments of the present invention have a mean ALGI for 150%, 175%, and 195% elongation of at least about 19 kg*mm, preferably at least about 21 kg*mm, more preferably at least about 24 kg*mm, more preferably at least about 27 kg*mm, and most preferably at least about 29 kg*mm.

While the invention has been described with reference to particularly preferred embodiments, other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A disposable absorbent garment comprising:
   a back sheet;
   a top sheet;
   an absorbent core at least partially disposed between the back sheet and the top sheet;
   at least one longitudinally extending, elasticized standing leg gather disposed laterally from a longitudinal centerline of the garment, the at least one standing leg gather including at least one elastic element for distributing elastic contractile forces; and
   wherein the at least one standing leg gather has a mean Total Leg Gasketing Index over three elongation cycles of at least about 4.75 kg*mm.

2. The garment of claim 1, wherein the at least one standing leg gather has a mean Total Leg Gasketing Index over three elongation cycles of at least about 5.5 kg*mm.

3. The garment of claim 1, wherein the at least one standing leg gather has a mean Total Leg Gasketing Index over three elongation cycles of at least about 7 kg*mm.

4. The garment of claim 1, wherein the at least one standing leg gather has a mean Total Leg Gasketing Index over three elongation cycles of at least about 8 kg*mm.

5. The garment of claim 1, wherein the elasticized standing leg gather includes at least 5 elastic elements.

6. The garment of claim 5, wherein the leg gather includes at least 7 elastic elements.

7. The garment of claim 1, wherein the elasticized standing leg gather has a height of from about 20 mm to about 100 mm.

8. The garment of claim 7, wherein the leg gather has a height of from about 35 mm to about 60 mm.

9. The garment of claim 1, wherein the elastic elements have a decitex (dtex) of between about 400 and about 1300.

10. The garment of claim 9, wherein the dtex is between about 680 and about 940.

11. A disposable absorbent garment comprising:
    a back sheet;
    a top sheet;
    an absorbent core at least partially disposed between the back sheet and the top sheet;
    at least one longitudinally extending, elasticized standing leg gather disposed laterally from a longitudinal centerline of the garment, the at least one standing leg gather including at least one elastic element for distributing elastic contractile forces; and
    wherein the at least one standing leg gather has a mean Summation Leg Gasketing Index at 150% elongation for three cycles of at least about 15 kg*mm.

12. The garment of claim 11, wherein the at least one standing leg gather has a mean Summation Leg Gasketing Index at 150% elongation for three cycles of at least about 21 kg*mm.

13. The garment of claim 11, wherein the at least one standing leg gather has a mean Summation Leg Gasketing Index at 175% elongation for three cycles of at least about 20 kg*mm.

14. The garment of claim 11, wherein the at least one standing leg gather has a mean Summation Leg Gasketing Index at 175% elongation for three cycles of at least about 30 kg*mm.

15. The garment of claim 11, wherein the at least one standing leg gather has a mean Summation Leg Gasketing Index at 195% elongation for three cycles of at least about 25 kg*mm.

16. The garment of claim 11, wherein the at least one standing leg gather has a mean Summation Leg Gasketing Index at 195% elongation for three cycles of at least about 35 kg*mm.

17. The garment of claim 11, wherein the elasticized standing leg gather includes at least 5 elastic elements.

18. The garment of claim 17, wherein the leg gather includes at least 7 elastic elements.

19. The garment of claim 11, wherein the elasticized standing leg gather has a height of from about 20 mm to about 100 mm.

20. The garment of claim 19, wherein the leg gather has a height of from about 35 mm to about 60 mm.

21. The garment of claim 11, wherein the elastic elements have a decitex (dtex) of between about 400 and about 1300.

22. The garment of claim 21, wherein the dtex is between about 680 and about 940.

23. A disposable absorbent garment comprising:
    a back sheet;
    a top sheet;
    an absorbent core at least partially disposed between the back sheet and the top sheet;
    at least one longitudinally extending, elasticized standing leg gather disposed laterally from a longitudinal centerline of the garment, the at least one standing leg gather including at least one elastic element for distributing elastic contractile forces; and
    wherein the at least one standing leg gather has a mean first cycle partial Average Leg Gasketing Index of at least about 23 kg*mm.

24. The garment of claim 23, wherein the at least one standing leg gather has a mean first cycle partial Average Leg Gasketing Index of at least about 30 kg*mm.

25. The garment of claim 23, wherein the at least one standing leg gather has a mean second cycle partial Average Leg Gasketing Index of at least about 19 kg*mm.

26. The garment of claim 23, wherein the at least one standing leg gather has a mean second cycle partial Average Leg Gasketing Index of at least about 28 kg*mm.

27. The garment of claim 23, wherein the at least one standing leg gather has a mean third cycle partial Average Leg Gasketing Index of at least about 19 kg*mm.

28. The garment of claim 23, wherein the at least one standing leg gather has a mean third cycle partial Average Leg Gasketing Index of at least about 27 kg*mm.

29. The garment of claim 23, wherein the elasticized standing leg gather includes at least 5 elastic elements.

30. The garment of claim 29, wherein the leg gather includes at least 7 elastic elements.

31. The garment of claim 23, wherein the elasticized standing leg gather has a height of from about 20 mm to about 100 mm.

32. The garment of claim 31, wherein the leg gather has a height of from about 35 mm to about 60 mm.

33. The garment of claim 23, wherein the elastic elements have a decitex (dtex) of between about 400 and about 1300.

34. The garment of claim 33, wherein the dtex is between about 680 and about 940.

35. A disposable absorbent garment comprising:

a back sheet;

a top sheet;

an absorbent core at least partially disposed between the back sheet and the top sheet;

at least one longitudinally extending, elasticized standing leg gather disposed laterally from a longitudinal centerline of the garment, the at least one standing leg gather including at least one elastic element for distributing elastic contractile forces; and wherein the at least one standing leg gather has a first cycle Leg Gasketing Index at 150% elongation of at least about 5.5 kg*mm.

36. The garment of claim 35, wherein the at least one standing leg gather has a first cycle Leg Gasketing Index at 150% elongation of at least about 8 kg*mm.

37. The garment of claim 35, wherein the at least one standing leg gather has a second cycle Leg Gasketing Index at 150% elongation of at least about 4.75 kg*mm.

38. The garment of claim 35, wherein the at least one standing leg gather has a third cycle Leg Gasketing Index at 150% elongation of at least about 4.5 kg*mm.

39. The garment of claim 35, wherein the at least one standing leg gather has a first cycle Leg Gasketing Index at 175% elongation of at least about 7.25 kg*mm.

40. The garment of claim 39, wherein the at least one standing leg gather has a first cycle Leg Gasketing Index at 175% elongation of at least about 11 kg*mm.

41. The garment of claim 39, wherein the at least one standing leg gather has a second cycle Leg Gasketing Index at 175% elongation of at least about 6.25 kg*mm.

42. The garment of claim 39, wherein the at least one standing leg gather has a third cycle Leg Gasketing Index at 175% elongation of at least about 6 kg*mm.

43. The garment of claim 39 wherein the at least one standing leg gather has a first cycle Leg Gasketing Index at 195% elongation of at least about 9.25 kg*mm.

44. The garment of claim 43, wherein the at least one standing leg gather has a first cycle Leg Gasketing Index at 195% elongation of at least about 13 kg*mm.

45. The garment of claim 43, wherein the at least one standing leg gather has a second cycle Leg Gasketing Index at 195% elongation of at least about 8.25 kg*mm.

46. The garment of claim 43, wherein the at least one standing leg gather has a third cycle Leg Gasketing Index at 195% elongation of at least about 8 kg*mm.

47. The garment of claim 35, wherein the elasticized standing leg gather includes at least 5 elastic elements.

48. The garment of claim 47, wherein the leg gather includes at least 7 elastic elements.

49. The garment of claim 35, wherein the elasticized standing leg gather has a height of from about 20 mm to about 100 mm.

50. The garment of claim 49, wherein the leg gather has a height of from about 35 mm to about 60 mm.

51. The garment of claim 35, wherein the elastic elements have a decitex (dtex) of between about 400 and about 1300.

52. The garment of claim 51, wherein the dtex is between about 680 and about 940.

53. An absorbent garment comprising:

a back sheet;

a top sheet;

an absorbent core at least partially disposed between the back sheet and the top sheet;

at least one longitudinally extending standing leg gather disposed laterally from a longitudinal centerline of the garment, the at least one leg gather including a first end portion, a middle portion, and a second end portion, and the at least one standing leg gather including at least one elastic element for distributing elastic contractile forces;

wherein the first end portion, the middle portion, and the second end portion are secured to the top sheet along a first longitudinally extending bond region;

wherein the first end portion is secured by a first end bond such that the first end portion is folded over onto itself; and wherein the second end portion is secured by a second end bond such that the second end portion is folded over onto itself; and wherein the at least one standing leg gather has a first cycle Leg Gasketing Index at 195% elongation of at least about 9.25 kg*mm.

54. The garment of claim 53, wherein the standing leg gather has a Total Leg Gasketing Index of at least about 4.75 kg*mm.

55. The garment of claim 53, wherein the first bond region includes a continuous bond region, a first partial bond region and a second partial bond region, and wherein the continuous bond region is disposed along a substantial portion of the longitudinal extent of the standing leg gathers, the first partial bond region is disposed along a substantial portion of a longitudinal extent of the first end portion and between the continuous bond section and the longitudinal centerline, and the second partial bond region is disposed along a substantial portion of a longitudinal extent of the second end portion and between the continuous bond section and the longitudinal centerline.

56. The garment of claim 53, wherein the standing leg gather includes at least seven elastics.

57. The garment of claim 53, wherein the elastics are comprised of an elastomer.

58. The garment of claim 53, wherein the elastics have a decitex of about 400 to about 1200.

59. The garment of claim 58, wherein the elastics have a decitex of about 680 to about 940.

60. The garment of claim 53, wherein the middle portion of the standing leg gather has a height of about 20 mm to about 100 mm.

61. The garment of claim 60, wherein the middle portion of the standing leg gather has a height of about 30 mm to about 70 mm.

62. A method of making an absorbent garment comprising:

providing a top sheet material to a garment forming station;

providing a back sheet material to a garment forming station;

providing an absorbent core to a garment forming station;

disposing the absorbent core between the top sheet material and the back sheet material at the garment forming station; and disposing on the top sheet material at least one longitudinally extending, elasticized standing leg gather laterally from a longitudinal centerline of the top sheet material, whereby the at least one standing leg gather includes at least one elastic element for distributing elastic contractile forces, wherein the at least one standing leg gather has a mean Total Leg Gasketing Index over three elongation cycles of at least about 4.75 kg*mm.

63. The method of claim 62, wherein the at least one standing leg gather has a mean Total Leg Gasketing Index over three elongation cycles of at least about 5.5 kg*mm.

64. The method of claim 62, wherein the at least one standing leg gather has a mean Total Leg Gasketing Index over three elongation cycles of at least about 7 kg*mm.

65. The method of claim 62, wherein the at least one standing leg gather has a mean Total Leg Gasketing Index over three elongation cycles of at least about 8 kg*mm.

66. The method of claim 62, wherein the elasticized standing leg gather includes at least 5 elastic elements.

67. The method of claim 66, wherein the leg gather includes at least 7 elastic elements.

68. The method of claim 66, wherein the elasticized standing leg gather has a height of from about 20 mm to about 100 mm.

69. The method of claim 68, wherein the leg gather has a height of from about 35 mm to about 60 mm.

70. The method of claim 62, wherein the elastic elements have a decitex (dtex) of between about 400 and about 1300.

71. The method of claim 70, wherein the dtex is between about 680 and about 940.

* * * * *